US011065312B2

(12) United States Patent
Breunig et al.

(10) Patent No.: US 11,065,312 B2
(45) Date of Patent: *Jul. 20, 2021

(54) VACCINATION BY MEANS OF RECOMBINANT YEAST BY PRODUCING A PROTECTIVE HUMORAL IMMUNE RESPONSE AGAINST DEFINED ANTIGENS

(71) Applicant: Martin-Luther-Universitaet Halle-Wittenberg, Halle (DE)

(72) Inventors: Karin Breunig, Halle/Saale (DE); Sven-Erik Behrens, Halle/Saale (DE)

(73) Assignee: VEROVACCiNES Gmbh, Halle (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/364,238

(22) PCT Filed: Dec. 12, 2012

(86) PCT No.: PCT/DE2012/001205

§ 371 (c)(1),
(2) Date: Oct. 6, 2014

(87) PCT Pub. No.: WO2013/107436

PCT Pub. Date: Jul. 25, 2013

(65) Prior Publication Data

US 2015/0190486 A1 Jul. 9, 2015

(30) Foreign Application Priority Data

Dec. 13, 2011 (DE) ..................... 10 2011 121 069.9

(51) Int. Cl.

*A61K 6/00* (2020.01)
*A61K 39/12* (2006.01)

(Continued)

(52) U.S. Cl.

CPC .......... *A61K 39/0002* (2013.01); *A61K 39/12* (2013.01); *C07K 14/005* (2013.01);

(Continued)

(58) Field of Classification Search

None

See application file for complete search history.

(56) References Cited

U.S. PATENT DOCUMENTS 5,830,463 A 11/1998 Duke et al.
8,778,358 B2 * 7/2014 Telford .............. A61K 39/0208 424/190.1

(Continued)

FOREIGN PATENT DOCUMENTS

| | | |
|---|---|---|
| EP | 1 752 468 | 2/2007 |
| WO | WO-90/15140 | 12/1990 |

(Continued)

OTHER PUBLICATIONS

Hodge. Carcinoembryonic antigen as a target for cancer vaccines. Cancer Immunol Immunother. Nov. 1996;43(3):127-34.*

(Continued)

*Primary Examiner* — Michelle S Horning
(74) *Attorney, Agent, or Firm* — Norris McLaughlin, P.A.

(57) ABSTRACT

The invention relates to recombinant yeasts of the *Kluyveromyces lactis* species for the production of a humoral immune response against defined antigens, to the production of said yeasts, and to the use thereof for protective vaccination against pathogens and malignant cells containing said antigens.

44 Claims, 13 Drawing Sheets

Specification includes a Sequence Listing.

(51) Int. Cl.

| | |
|---|---|
| ***A61K 39/00*** | (2006.01) |
| ***C12N 15/81*** | (2006.01) |
| ***C07K 14/005*** | (2006.01) |
| ***C12N 7/00*** | (2006.01) |
| ***G01N 33/68*** | (2006.01) |

(52) U.S. Cl.

CPC ............ *C12N 7/00* (2013.01); *C12N 15/815* (2013.01); *G01N 33/6854* (2013.01); *A61K 2039/521* (2013.01); *A61K 2039/552* (2013.01); *A61K 2039/55566* (2013.01); *C12N 2720/10034* (2013.01); *Y02A 50/30* (2018.01)

(56) References Cited

U.S. PATENT DOCUMENTS

| | | | | |
|---|---|---|---|---|
| 9,885,052 | B2 * | 2/2018 | Breunig ................. | A61K 39/12 |
| 2007/0166323 | A1 | 7/2007 | Duke et al. | |
| 2007/0212375 | A1 | 9/2007 | Caston et al. | |
| 2009/0304741 | A1 | 12/2009 | Duke et al. | |

FOREIGN PATENT DOCUMENTS

| | | |
|---|---|---|
| WO | WO-2006/044923 | 4/2006 |
| WO | WO-2007/092792 | 8/2007 |
| WO | WO-2010/054649 | 5/2010 |
| WO | WO-2011/032119 | 3/2011 |

OTHER PUBLICATIONS

Wang YC1, Chuang LL, Lee FW, Da Silva NA. Sequential cloned gene integration in the yeast Kluyveromyces lactis. Appl Microbiol Biotechnol. Oct. 2003;62(5-6):523-7. Epub May 21, 2003. (Year: 2003).*

Kooistra et al. Efficient gene targeting in Kluyveromyceslactis. Yeast 2004; 21: 781-792. (Year: 2004).*

Villegas Pedro, et al: "Infectious Bursal Disease Subunit Vaccination", Avian Diseases Dec. 2008, vol. 52, No. 4., Dec. 2008 (Dec. 2008), pp. 670-674.

Pitcovski J., et al: "Development and large-scale use of recombinant VP2 vaccine for the prevention of infectious bursal disease of chickens", Vaccine, Elsevier Ltd. GB. vol. 21, No. 32, Dec. 1, 2003 (Dec. 1, 2003), pp. 4736-4743.

Stubbs A. C., et al: "Whole recombinant yeast vaccine activates dendritic cells and elicits protective cell-mediated immunity", Nature Medicine, Nature Publishing Group, New York, NY, US, vol. 7, No. 5, May 1, 2001 (May 1, 2001), pp. 625-629.

Stubbs A. C., et al: "Recombinant yeast as a vaccine vector for the induction of cytotoxic T-lymphocyte responses", Current Opinion in Molecular Therapeutics, Current Drugs, London, GB, vol. 4, No. 1, Feb. 1, 2002 (Feb. 1, 2002), pp. 35-40.

Bathurst I. C.: "Protein Expression in Yeast as an Approch to Production of Recombinant Malaria Antigens", American Journal of Tropical Medicine & Hygiene, American Society of Tropical Medicine and Hygiene, US, vol. 50, No. 4, Suppl., Jan. 1, 1994 (Jan. 1, 1994), pp. 20-26.

Arnold Marina, et al: "Protective Vaccination against Infectious Bursal Disease Virus with Whole Recombinant *Kluyveromyces lactis* Yeast Expressing the Viral VP2 Subunit", PLOS ONE, vol. 7, No. 9, Sep. 2012 (Sep. 2012), pp. 1-11.

Jorrit-Jan Krijger, et al: "A novel, lactase-based selection and strain improvement strategy for recombinant protein expression in Kluyveromyces lactis", Microbial Cell Factories, Biomed Central, London, NL, vol. 11, No. 1, Aug. 20, 2012 (Aug. 20, 2012), pp. 1-12.

Wansley Elizabeth K., et al: "Vaccination with a Recombinant *Saccharomyces cerevisiae* expressing a Tumor Antigen Breaks Immune Tolerance and Elicits Therapeutic Antitumor Responses", Clinical Cancer Research, vol. 14, No. 13, Jul. 1, 2008 (Jul. 1, 2008), pp. 4316-4325.

* cited by examiner

Figure 4D

| | Group | ELISA | Virus neutralization number positive |
|---|---|---|---|
| Feeding | VP2 Yeast | 0.13 ± 0.031 | 40 % |
| | Control yeast | 0.11 ± 0.006 | 0 % |
| Subcutaneous | VP2 Yeast | 0.22 ± 0.05 | 100 % |
| | Control yeast | 0.13 ± 0.015 | 0 % |

Figure 5C

| | Group | ELISA (Title) | Virus neutralization | Mortality | Lesions Score |
|---|---|---|---|---|---|
| Feeding | VP2 Yeast, short (9) | 1 | 6.89 ± 5.75 | 0/9 | 4, 4, 4, 4, 4, 4, 4, 4, 4 |
| | Control yeast, short (8) | 1 | 0 | 3/8 | 4, 4, 4, 4, 4, 4, 4, 4, 4 |
| | Mock, short (10) | 1 | 1.6 ± 5.06 | 1/10 | 4, 4, 4, 4, 4, 4, 4, 4, 4, 4 |
| | VP2 Yeast, long (9) | 35.56 ± 36.12 | 7.56 ± 5.08 | 0/9 | 1, 4, 4, 4, 4, 4, 4, 4, 4 |
| | Control yeast, long (10) | 9.4 ± 19.6 | 2 ± 2.91 | 1/10 | 4, 4, 4, 4, 4, 4, 4, 4, 4, 4 |
| | Mock, long (10) | 4 ± 2.58 | 0 | 0/10 | 4, 4, 4, 4, 4, 4, 4, 4, 4, 4 |
| | VP2 Yeast, long, Saponin (10) | 68.8 ± 70.87 | 6.8 ± 5.46 | 0/10 | 2, 4, 4, 4, 4, 4, 4, 4, 4, 4 |
| | Control yeast, long, Saponin (9) | 33.7 ± 38 | 0.89 ± 1.76 | 1/9 | 4, 4, 4, 4, 4, 4, 4, 4, 4 |
| | Mock, long, Saponin (9) | 1 | 0 | 0/9 | 4, 4, 4, 4, 4, 4, 4, 4, 4 |
| Subcutaneous | VP2 Yeast (5) | 2707 ± 823.4 | 3072 ± 1448.2 | 0/5 | 1, 1, 1, 1, 3 |
| | Control yeast (5) | 1 | > 8 | 1/5 | 4, 4, 4, 4, 4, 4 |
| | PBS (5) | 1 | > 8 | 1/5 | 4, 4, 4, 4, 4, 4 |

VACCINATION BY MEANS OF RECOMBINANT YEAST BY PRODUCING A PROTECTIVE HUMORAL IMMUNE RESPONSE AGAINST DEFINED ANTIGENS

BACKGROUND OF THE INVENTION

The invention relates to recombinant yeasts for the creation of a humoral immune response against defined antigens, the production of these yeasts and the use thereof for protective vaccination against pathogens and malignant cells which contain these antigens.

Vaccines are used to prevent diseases (preventive vaccines) or to treat established diseases (immunotherapeutic vaccines). In the last 100 years preventive vaccines have significantly contributed to the reduction of infectious diseases. Immunotherapeutic vaccines have only been developed and used for about 20 years, for example against persistent infections with viruses, bacteria or parasites or against carcinogenic diseases. The purpose of the vaccination is to induce a cellular (i.e. essentially T and NK cell-mediated) and/or humoral (i.e. essentially B cell/antibody-mediated) immune response and an immunological memory towards antigenic components of pathogens or malignant (tumorigenic) cells.

Classical vaccines contain the whole pathogen in attenuated (inactivated) or killed form, including its genetic material, nucleic acids in the form of DNA or RNA. For their production, these classical vaccines mostly require special safety precautions and/or the use of experimental animals and/or the use of cell cultures; in addition, they often need to be expensively stored and transported with the use of cold chains. Further, they involve the risk that substances from their production (e.g. from the experimental animal or from the cell culture) create side-effects in the vaccinated individual or that undesired reactivations of the pathogen occur. Problems also exist in diagnosis: thus for example in the case of the vaccination of livestock, vaccinees cannot be distinguished from naturally infected animals, so that the early warning system which is based on the detection of fresh infections can fail. Hence so-called “sub-unit” vaccines which only contain parts of the pathogen were developed. A prerequisite for this is that “main antigens” of the particular pathogen are known. Main antigens are mostly surface components of the pathogen which can be recognized by the immune system, e.g. proteins of a viral envelope or of the virus capsid. Even in the absence of a complete virus particle, these can induce a humoral and/or a cellular immune response and an immunological memory in the host against the virus. Since in “subunit vaccination” typical components of the pathogen are missing, vaccinated individuals can be distinguished from those naturally infected by a differential diagnosis; hence reference is also made to a “subunit marker vaccine”. Disadvantages of many subunit vaccines often are costly production and inadequate immunogenicity. While the pathogens themselves can be efficiently cultured (with the aforesaid limitations), their main antigens must be produced by genetic engineering by cost-intensive and mostly inefficient processes and laboriously purified. Accordingly, the common subunit vaccines are often sensitive, have to be stored refrigerated and have a low stability. For these reasons, a large proportion of mass-produced vaccines are still based on the classical principle with complete pathogens. For example, most vaccines directed against the world-wide poultry disease infectious bursitis (IBD) are currently in the majority based on attenuated (weakened) or inactivated viruses of the IBD-triggering infectious bursitis virus (IBDV).

Attempts are being made to compensate the problem of weaker immunogenicity with subunit vaccines through the additional use of adjuvants. Adjuvants are substances which have empirically been found to be immunostimulating. They strengthen the immune response non-specifically and often in a little understood way. So far, only a few adjuvants are approved for human use. The only additives which are for example approved in the USA for use in people are aluminum salts, aluminum hydroxide and aluminum phosphate. However, aluminum salt formulations cause additional problems in the storage of the corresponding vaccine. In addition, these adjuvants do not exhibit adequate efficacy with all antigens.

The genetic engineering production of foreign proteins, which include most subunit vaccines, can be effected in various host cells. As well as the intestinal bacterium *Escherichia coli*, mammalian cells which can be proliferated in cell cultures, plant cells and various fungi are established as host systems. Microbial systems such as bacteria and fungi can be particularly inexpensively grown on a large scale. Yeast cells of the yeast genera *Saccharomyces, Pichia* and *Kluyveromyces* have already for decades been routinely used for the expression of foreign proteins. Compared to bacteria, yeast cells have the advantage that they are eukaryotes, i.e. they are in many ways similar to the animal cells, and eukaryotic proteins, i.e. proteins which are formed and/or have to be functional in animal cells can be inexpensively produced in yeasts in natural or almost natural form (Bathurst, 1994; Gellissen & Hollenberg, 1997). Yeasts were at first only used for producing the foreign proteins, and the proteins were purified from the yeast cells and used as subunit vaccines. Only recently have attempts been made to administer yeasts themselves or cell fractions of the yeasts as vaccines.

For about the last 5 years, attempts have been made to use *Saccharomyces cerevisiae* (“baker’s yeast”, *S. cerevisiae*) itself for vaccination: thus it could be shown that dendritic cells can be activated and antigen-specific T cell immune responses, especially cytotoxic T cell immune responses against certain antigens, can be created by subcutaneously administered antigen-expressing cells of *S. cerevisiae*. This cellular immune response was found to be protective against the administration of certain tumor cells, i.e. following the vaccination fewer tumors appeared in vaccinated animals than in control animals. This method is currently also being tested in immunotherapeutic applications in tumor diseases (Stubbs et al., 2001; Lu et al., 2004).

The following sources from the prior art, in which a yeast-based vaccination is described, are well-known to those skilled in the art:

A number of US patents, e.g. 20090304741, U.S. Pat. No. 5,830,463 and 10738646 and 20070166323 describe the use of *S. cerevisiae* which contain at least one recombinant antigen in immunotherapy. It was shown that these yeasts are effective in stimulating an immune reaction, in particular a cell-mediated immune reaction.

WO/2006/044923 discloses yeast (*S. cerevisiae*) which recombinantly expresses various proteins of the hepatitis C virus (HCV) and which can trigger an immune reaction, mainly a T cell response, against these HCV proteins and is intended for use as a vaccine against chronic hepatitis C.

WO/2007/092792 describes the possible use of recombinant *S. cerevisiae* against influenza virus infections, wherein a combination of various yeast strains is used whose administration results in T cell induction, i.e. a cellular immune response.

WO/2011/032119 relates to a method for improving the efficacy of a yeast-based immunotherapy in patients. The method comprises a yeast-based agent which modulates the production or the survival of CD4+ TH17 cells.

In none of the available patents is yeast demonstrably used for the induction of a protective humoral immune response against infectious diseases or tumors (subject of this application). Furthermore, either the yeasts *S. cerevisiae* or *Pichia pastoris* were used, but not *Kluyveromyces lactis* (subject of this application).

Like *S. cerevisiae*, the "milk yeast" *Kluyveromyces lactis* (*K. lactis*) also has GRAS status (GRAS: generally regarded as safe), i.e. it is suitable for use in animals or man (van Ooyen et al., 2006). Although morphologically very similar to the baker's yeast *S. cerevisiae*, the evolutionary lines of the two genera have developed in different directions from a common ancestor more than 100 million years ago. Hence *K. lactis* differs fundamentally from *S. cerevisiae* in many properties. Some of these differences are of great importance for usability in biotechnological applications. The evolution of *S. cerevisiae* entailed the specialization of the metabolism on alcoholic fermentation and hence the loss of many ancestral genes. However, alcoholic fermentation is not typical for most yeasts. It takes place in *S. cerevisiae* at high glucose concentrations even when oxygen is present, conditions where the mitochondrial respiration would actually allow a much more efficient energy yield from sugar conversion: the function of the mitochondria, the "power houses" of the cell, is largely suppressed by "glucose repression". *K. lactis* differs considerably from *S. cerevisiae* in the regulation of the function of the mitochondria (Chen and Clark-Walker, 1995, Clark-Walker, 2007). In contrast to *S. cerevisiae, K. lactis* belongs to the so-called "Crabtree negative" yeasts. Such yeasts as a rule form no ethanol under strictly aerobic conditions, but rather via mitochondrial activity degrade the glucose completely to $CO_2$ with formation of ATP. This physiological property is of fundamental importance, since it leads to a marked increase in the biomass yield in large-scale fermentations, which results in a marked cost decrease in the utilization of these yeasts as producers of recombinant proteins. Moreover, studies in *K. lactis* have shown that mutations in the hexose kinase-mediated glucose signaling pathway can improve the expression of heterologous genes (Donnini et al., 2004). Reduced glucose repression, especially of respiratory genes, is a feature of the "Crabtree negative" yeasts and could be connected with the empirically observed better foreign gene expression in such yeasts.

*K. lactis* and *S. cerevisiae* also exhibit considerable differences in the composition of the cell wall glucans (Backhaus et al., 2011); presumably these differences are based on different glycosyl transferases in the Golgi apparatus, which are involved in the maturation of glycoproteins: thus glycoproteins in *S. cerevisiae* contain multiple mannose phosphates, and the glycoproteins in *K. lactis* mainly terminal N-acetylglucosamines (Raschke and Ballou, 1972). It is to be assumed that these differences between *S. cerevisiae* and *K. lactis* in the glycosylation and secretion of proteins and in cell wall synthesis have a considerable influence on the intracellular location, folding and stability and thus also on the immunogenicity of heterologously expressed foreign proteins (Uccelletti et al., 2004).

WO/2010/054649 describes the production of a recombinant system from *K. lactis*. In the application examples given there, recombinant strains which were derived from the strain VAK367-D4 were used for mucosal or oral vaccination against various antigens. However, a disadvantage of oral/mucosal vaccination is that the vaccines must be used in large quantities in order to achieve a protective immunization.

BRIEF DESCRIPTION OF THE DRAWINGS

FIG. 4D is a tabular illustration of vaccination in mice;

FIG. 5C is a tabular illustration of vaccination in chickens; and

DETAILED DESCRIPTION OF THE INVENTION

Figure 1:
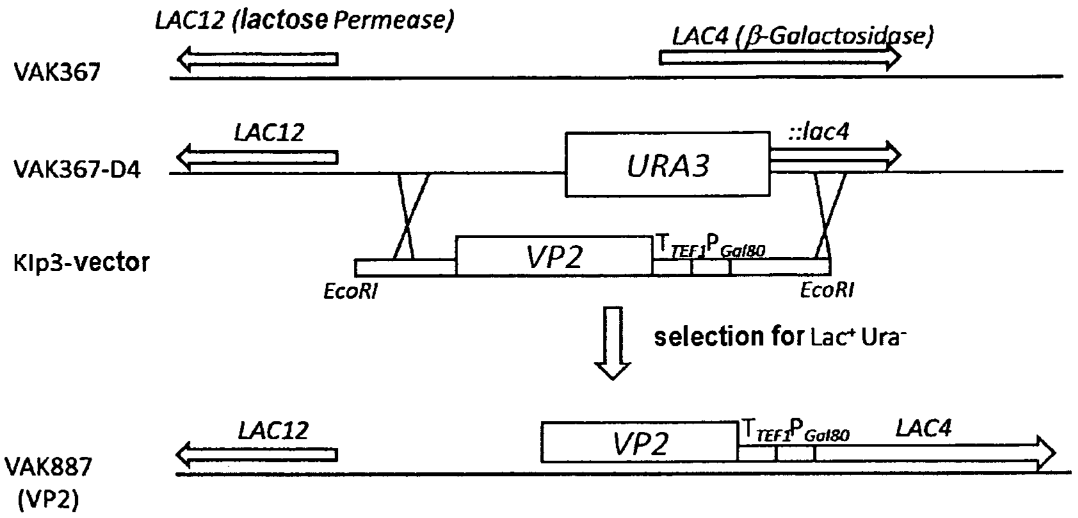
FIG. 1 is a schematic representation of the production of a vaccine strain.

FIG. 1 is a schematic representation of the production of the vaccine strain VAK887, which bears the IBDV VP2 foreign gene, by homologous recombination in the VAK367-D4 starting strain. Via transformation of the plasmid KIp3-MCS (SEQ ID No.10) which contained the VP2 gene of the IBDV strain D78, the VP2 foreign gene was inserted by homologous recombination into the chromosomal LAC4 gene locus, which had been destroyed by insertion of the URA3 gene. During the recombination into the host genome the URA3 gene was replaced by the VP2 gene and the LAC4 gene was restored; recombinant yeast strains could be obtained by selection on lactose medium without uracil. Thereafter, expression of LAC4 (β-galactosidase) is controlled via the KIGAL80 promoter, and expression of the VP2 gene via the LAC4 promoter.

Figure 2A:
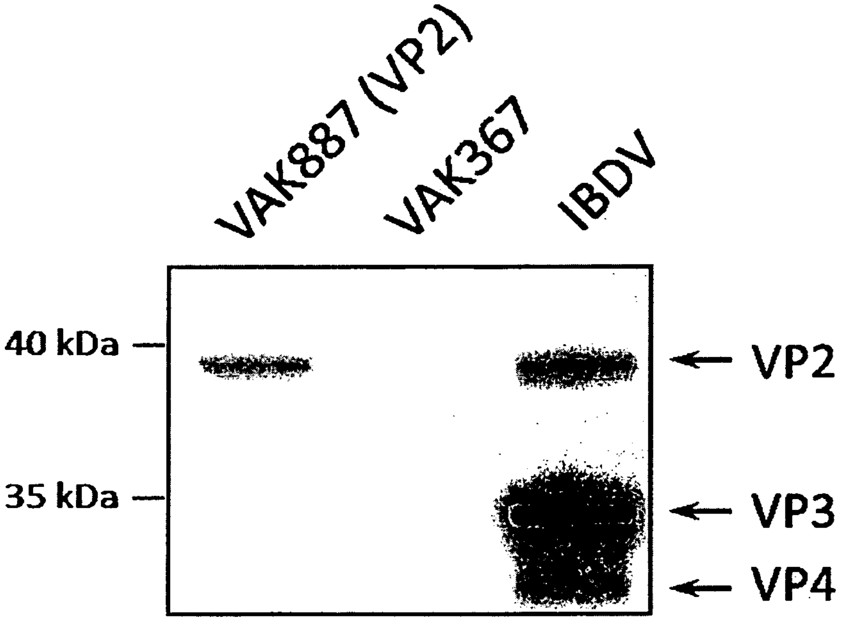
FIGS. 2A, 2B, 3A and 3B show Western blot tests.
Figure 2B:
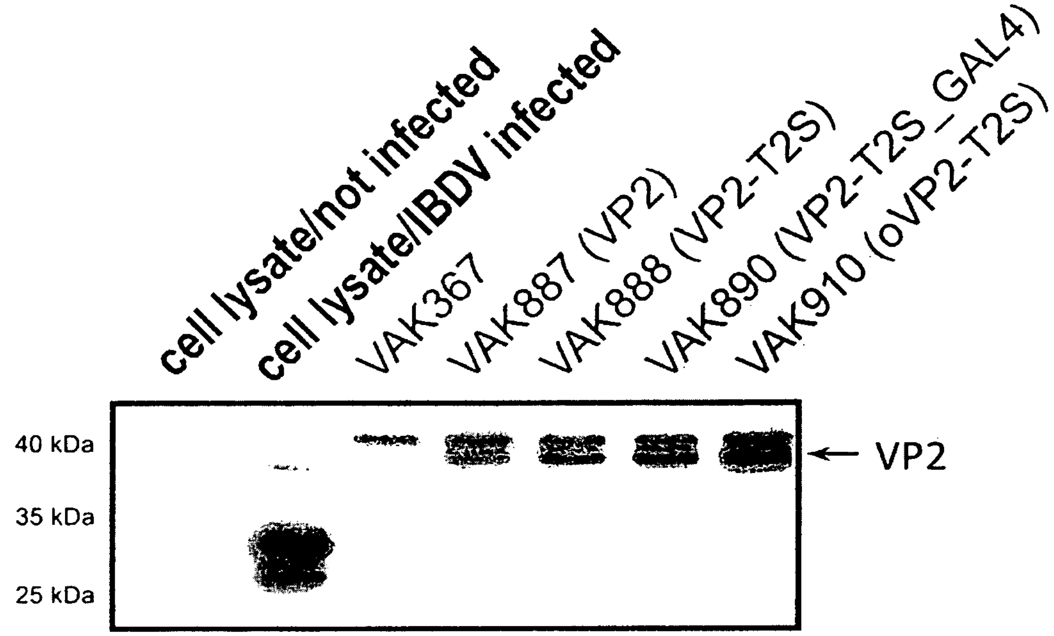

FIG. 2A shows the expression of IBDV VP2 by the strain VAK887 in comparison to the original strain (VAK367) and in comparison to IBDV-infected chicken cells by Western blot analysis with a VP2-specific antibody. FIG. 2B shows the expression analysis of recombinant IBDV VP2 and mutated IBDV VP2-T2S in various VP2-expressing *K. lactis* variants. The original *K. lactis* variant VP2 (VAK887) expressed only moderate quantities of viral protein. The VP2 expression could be increased in the strain *K. lactis* VP2-T2S (VAK888) by replacing threonine at amino acid position 2 of the VP2 protein with serine. A further increase could be achieved by increasing the KIGAL4 gene dose (VP2-T2S_GAL4=VAK890) or by use of a yeast codon-optimized synthetic VP2 gene (oVP2-T2S=VAK910).

Figure 3A:
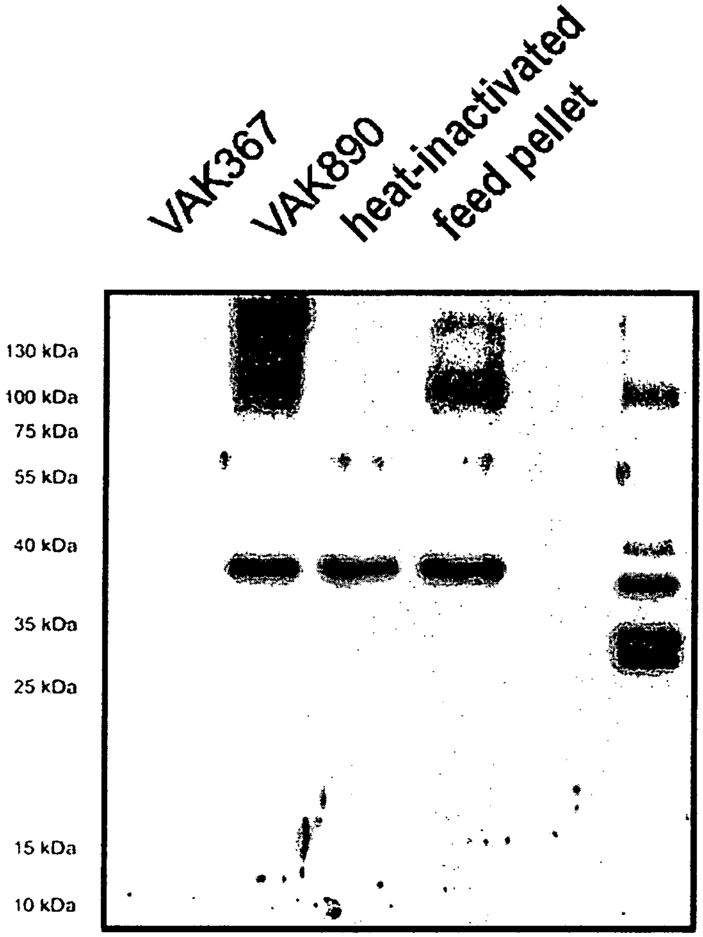
Figure 3B:
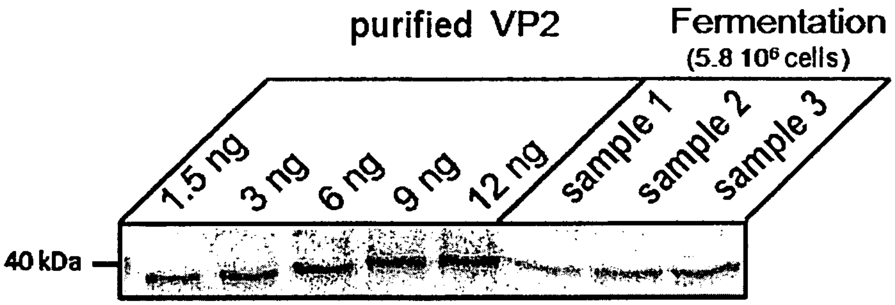
Figure 3C:
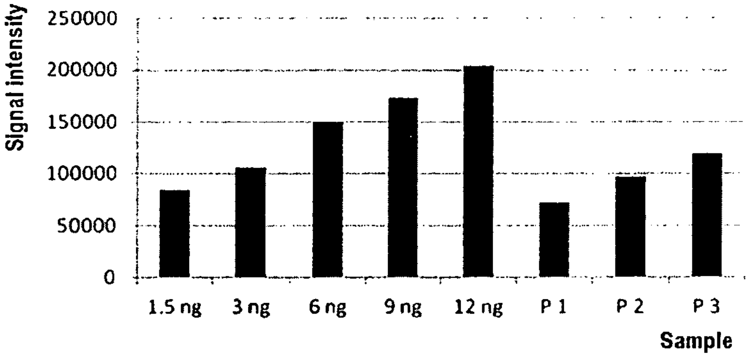
FIG. 3C is a bar graph of the densitometry results of the Western blot tests of FIG. 3B.

FIG. 3A shows that heat inactivation of the yeasts according to the invention at 90° C. for 2 hours does not lead to a loss of the recombinant VP2-T2S protein. Equal quantities of protein from non-inactivated yeast, inactivated yeast and yeast from a feed pellet were each separated on an SDS PAGE and tested in a Western blot with an anti-VP2 antibody in comparison to cell lysates from poultry cells which were or were not infected with IBDV. FIG. 3 further shows that the quantity of VP2-T2S in the variant VAK890 is ca. 0.7 fg heterologous protein per yeast cell (FIG. 3B). Here, defined quantities of purified VP2-T2S in comparison to VP2 from a defined cell count of *K. lactis* (strain VAK890) grown in the fermenter were stained in the Western blot and the result assessed by densitometry (FIG. 3C).

Figure 4A:
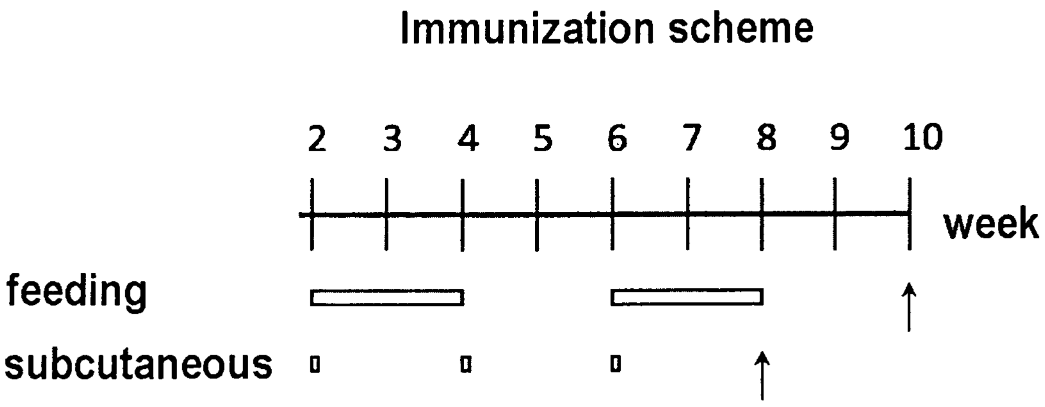
FIGS. 4A, 4B and 4C are graphical illustrations of vaccination in mice.
Figure 4B:
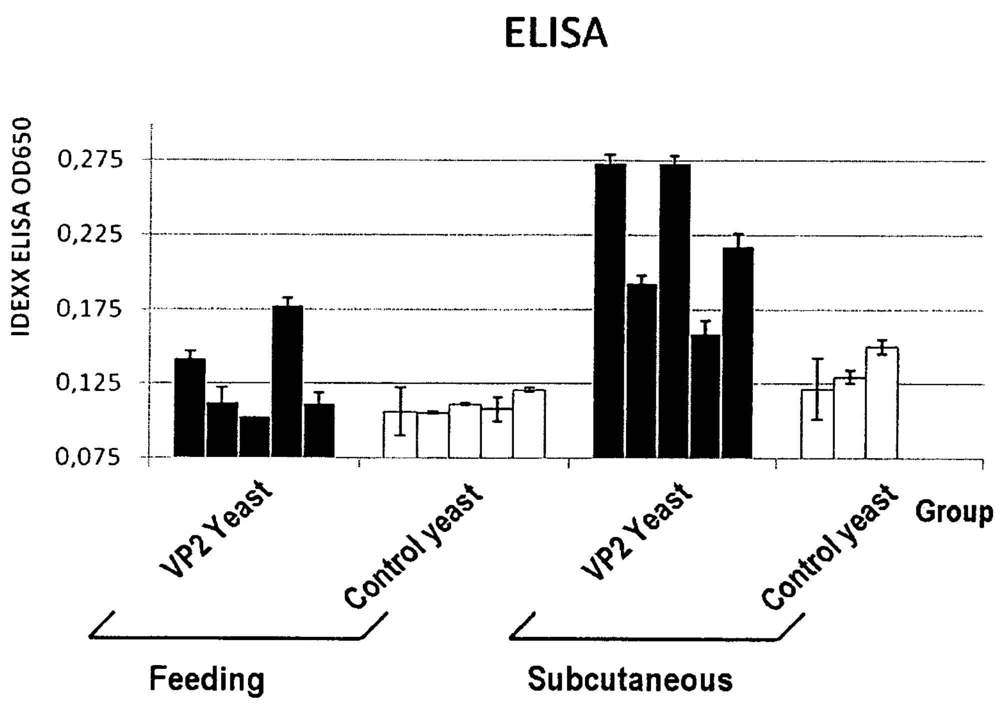
Figure 4C:
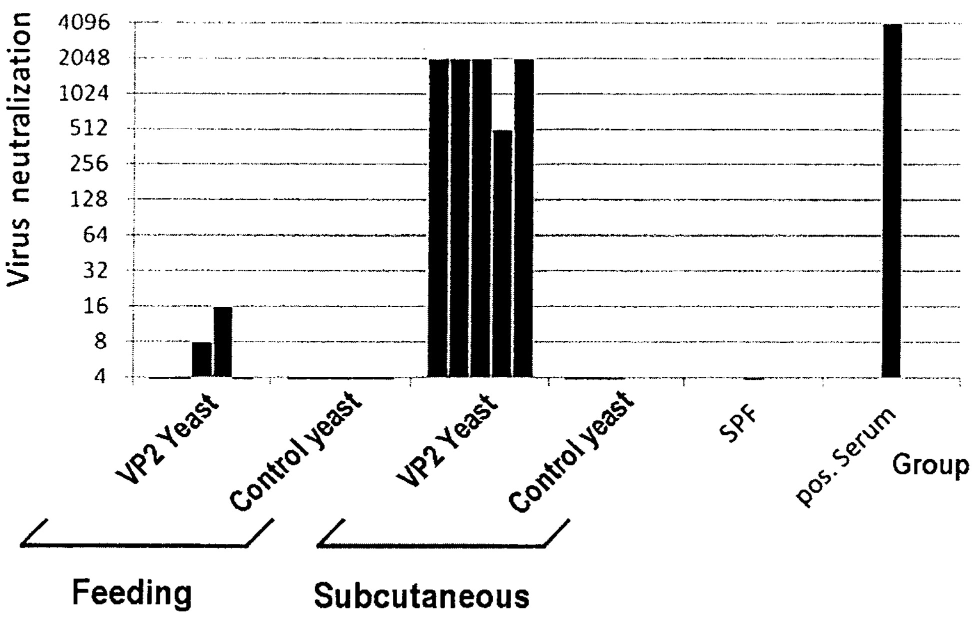

FIGS. 4A, 4B, 4C, 4D illustrate the vaccination in mice with subcutaneously administered, heat-inactivated, complete yeast cells of the *K. lactis* variant VAK890 in comparison to oral vaccination with complete yeast cells of the *K. lactis* variant VAK890. FIG. 4A shows the immunization scheme: subcutaneous immunization was effected three times, with two weeks pause each time; in comparison, feeding was effected twice for two weeks. Two weeks (arrow) after the last yeast administration, serum samples from the treated mice were tested for the presence of anti-VP2 antibodies in an IBDV-specific ELISA (FIG. 4B) and in an IBDV neutralization assay (FIG. 4C). FIG. 4D summarizes the fact that mice which were treated with VP2-expressing *K lactis* (strain KI VP2-T2S_GAL4 (VAK890)) exhibit higher titers of antibodies/neutralizing antibodies than mice which were treated with *K. lactis* wild type (strain VAK367). Further, it was shown that mice that were subcutaneously administered *K. lactis* (strain VAK890) exhibited markedly higher levels of antibodies/neutralizing antibodies than mice which were fed with *K. lactis* (strain VAK890). However, mice which were orally immunized with *K lactis* (strain 890) also showed an elevated titer of antibodies/neutralizing antibodies in comparison to mice which were treated with *K. lactis* wild type (strain VAK367).

Figure 5A:
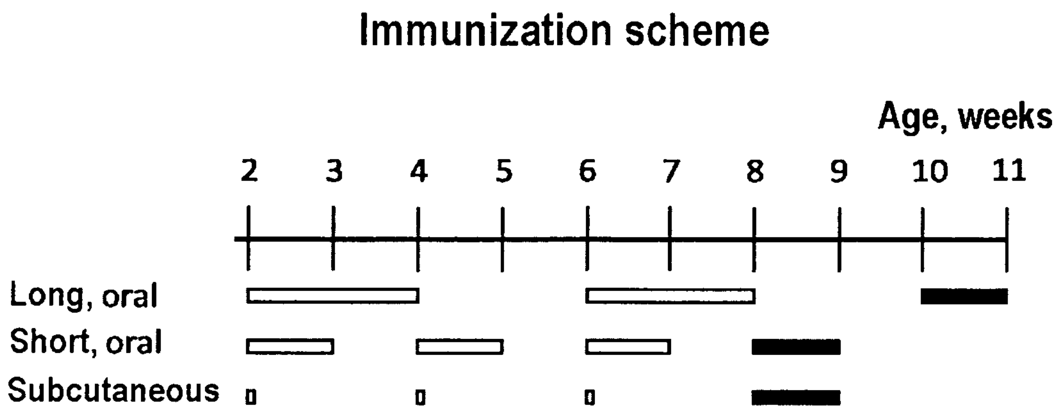
FIGS. 5A and 5B are graphical illustrations of vaccination in chickens.
Figure 5B:
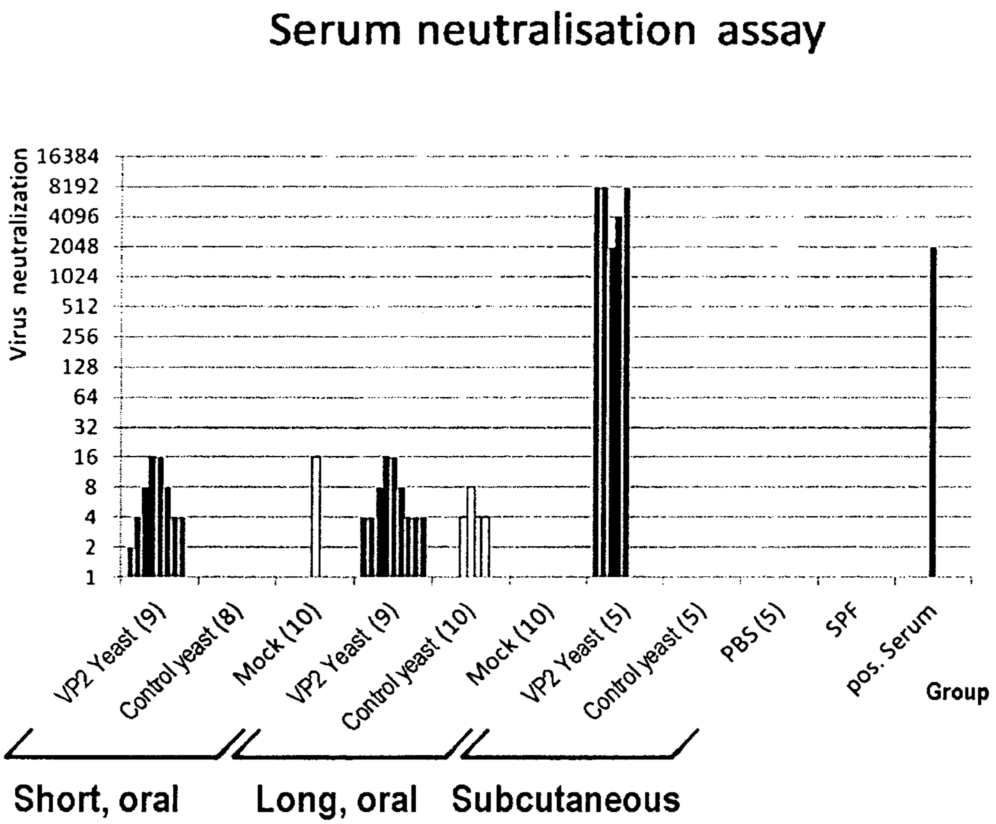

FIGS. 5A, 5B, 5C show the oral and subcutaneous vaccination in chickens with heat-inactivated, complete yeast cells of the *K lactis* variant VP2-T2S_GAL4 (VAK890). For the oral vaccination, either a short 1/1/1/1 scheme (1 week feed, 1 week pause, 1 week feed, etc.) or a longer 2/2/2 scheme was used (FIG. 5A). After 1 week or 2 weeks pause respectively after the vaccination, all treated animals were infected with IBDV (Edgar strain) at a concentration of 100 EID50 per animal (virus challenge: black bars). After oral vaccination, particularly after use of the extended treatment scheme, increased titers of virus-neutralizing antibodies could be detected in several animals. In contrast to this, the subcutaneous vaccination with recombinant *K. lactis* created high titers of virus-neutralizing antibodies in all treated animals (FIGS. 5B & C; IBDV-specific ELISA, IBDV neutralization assay). None of the animals treated with recombinant *K lactis* yeast died after infection with IBDV, irrespective of which treatment scheme was used. In contrast to this, the mortality rate was 10-35% in the control group (FIG. 5C). Analysis of lesions in the bursae of the treated animals showed that about 10% of the orally treated animals after use of the extended treatment scheme showed no signs of a viral infection after inoculation with IBDV: for this a so-called “lesions” score was used—scores 1 and 2 indicate bursae damaged not at all or a little; scores 3 and 4 indicate damaged and severely damaged bursae. As shown, all animals in which the recombinant *K lactis* strain VAK890 was subcutaneously administered exhibited complete protection against IBDV infection (FIG. 5C).

Figure 6:
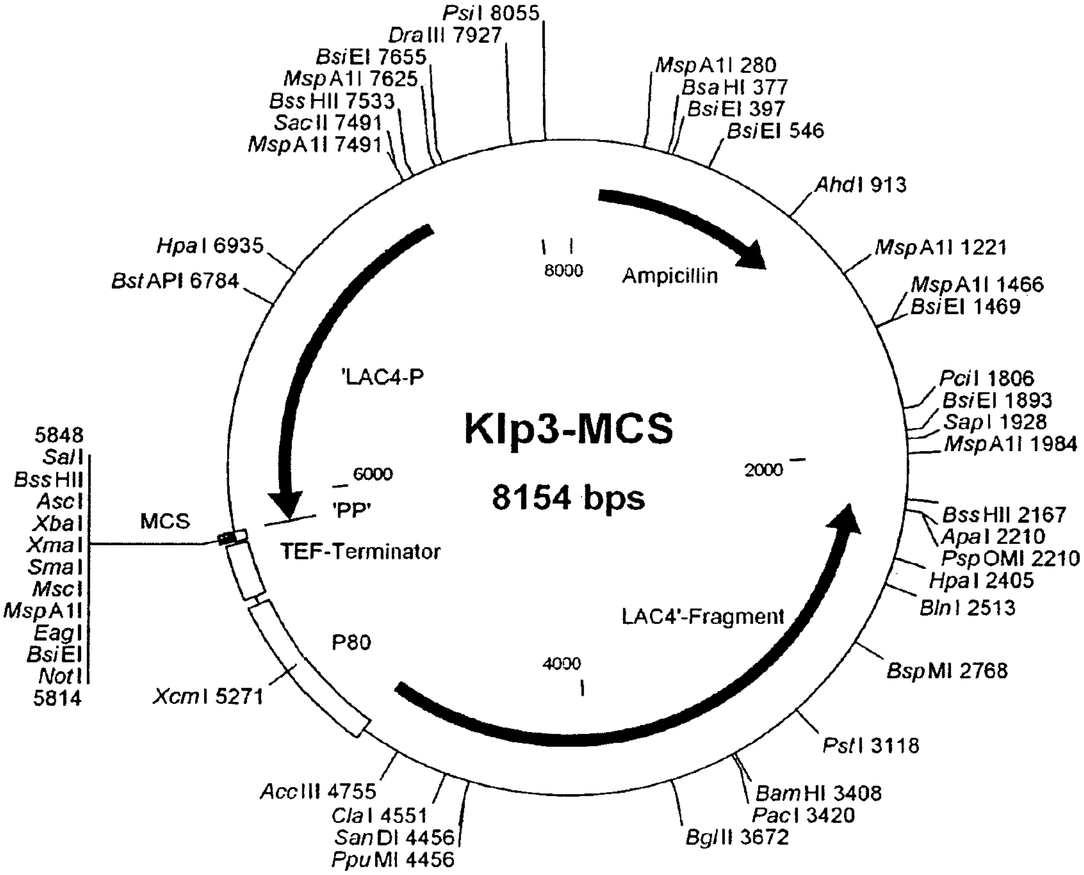
FIG. 6 is a schematic illustration of a vector.

FIG. 6 is a schematic representation of the structure of the vector KIp3-MCS (SEQ ID No.10).

The possibility of using recombinant yeasts for subcutaneous vaccination is known to those skilled in the art from the prior art: Stubbs et al., (2001) Nat. Med. 7: 625-629; Stubbs and Wilson (2002) Curr. Opin. Mol. Ther. 4: 35-40; Wansley et al., (2008) Clin. Cancer Res. 14: 4316-4325; U.S. Pat. No. 5,830,463, WO/2006/044923; WO/2007/092792 and WO/2011/032119. However, in the practical examples of these publications the work was performed exclusively with the yeast *Saccharomyces cerevisiae*. “Yeast” is a collective term for eukaryotic microorganisms growing as single cells, some with very different properties owing to divergent evolution over hundreds of millions of years (ca. 100 million years for *S. cerevisiae* and *K. lactis*). Thus in the use of *S. cerevisiae* and *K. lactis* for vaccination purposes in higher eukaryotes such as animal or man it is to be assumed that an immune response triggered by *S. cerevisiae* will differ markedly from an immune response triggered by *K. lactis*. This applies both for the immune response to foreign antigens expressed in the yeast and also for the immune response against endogenous yeast antigens. In the case of subcutaneous immunizations with complete *S. cerevisiae* cells, T cell induction i.e. a cellular immune response, was created. A protective, humoral immune response against an antigen with recombinant *S. cerevisiae* in simple ways (e.g. by direct administration of a single antigen-expressing strain) had not previously been confirmed in the prior art.

Starting from the background presented above, the problem was thus to provide a method with which a protective, humoral response against defined antigens can be created. A further problem comprised producing a subunit marker vaccine with which it is possible to distinguish vaccinated individuals from those naturally infected. A further problem comprised producing a subunit marker vaccine which simultaneously exhibits strong adjuvant properties and which is thus strongly immunogenic.

These problems were solved by provision of a yeast-based expression system which allows the targeted integration of foreign genes into the yeast genome. Recombinant yeasts which express foreign genes can be rapidly produced (i.e. within a few weeks) with this system. The yeasts can be inexpensively proliferated in the fermenter in large quantities (e.g. kilogram (kg) range). By regulated expression and fermentation in the fed batch process, cytotoxic antigens can also be expressed in this yeast system. After expression of the foreign gene, the yeast is heat-inactivated and can then be stored and transported unrefrigerated as a powder. The yeast powder can be used as a subunit marker vaccine directly, i.e. without further fractionation, either as an emulsion or as pellets (see practical examples). The antigen formulation and the adjuvant effect necessary for effective, i.e. protective, immunization are ensured by two factors: (i) by the possibility of targeted genetic modification of the expressed foreign protein and (ii) through the expression of the foreign protein in the yeast and the direct use of the yeast in oral or subcutaneous form; the yeast itself has a strong adjuvant effect. Subcutaneous administration is preferred. A recombinant yeast strain was produced; this expresses a specific viral antigen and can be used for subcutaneous vaccination in the method according to the invention. Complete preventive protection against an infection by the virus concerned was achieved. In the process, only very small quantities of yeast (e.g. in the milligram (mg) range in case of subcutaneous use in poultry) were used. Only 2-3 applications were necessary in order to achieve this protection.

The method according to the invention is suitable for use both in human medicine and also the veterinary medicine field. Use of the method according to the invention in the veterinary medicine field is preferred.

The method according to the invention is performed with yeasts. Suitable yeasts are for example yeasts of the genera *Saccharomyces* spec., *Pichia* spec. and *Kluyveromyces* spec. In a preferred embodiment, the method according to the invention is performed with yeasts of the genus *Saccharomyces* spec. and *Kluyveromyces* spec. Particularly preferred here is the use of *Saccharomyces cerevisiae* and *Kluyveromyces lactis*.

In the most preferred embodiment, the method according to the invention is performed with the yeast *Kluyveromyces lactis*.

The yeast *K. lactis* belongs to the so-called “food grade” yeasts, which have GRAS status (GRAS: generally regarded as safe). Like the baker’s yeasts, which have been tried and tested as food additives over millennia, the yeast *K. lactis* often present in dairy products is also regarded as harmless for the food industry.

As well as the possibility for fermentation explained under “prior art”, the yeast *K. lactis* has numerous advantages compared to *S. cerevisiae* as regards the expression of heterologous genes. *K. lactis* belongs to the so-called “petite negative” yeasts, that is, the loss of the mitochondrial DNA is lethal (because of the collapse of the mitochondrial membrane potential) (Chen et al., 1995; Clark-Walker, 2007). The mitochondrial function is closely coupled to $Ca^{2+}$-dependent signal transmission, production of reactive oxygen compounds, the stress response of the cell, protein glycosylation and cell wall integrity. As a result, the mitochondrial function decisively influences the production of recombinant glycoproteins and the composition of the cell wall.

In yeasts and mammals, the first steps of the N-glycosylation of proteins, which takes place in the endoplasmic reticulum, are the same. However, the steps taking place in the Golgi apparatus differ from each other. The glycosyl transferases present in the Golgi apparatus are different in the different yeast species. This results in differences in the composition of the glycoproteins in the cell wall. In *K. lactis*, the glycoproteins have terminal N-acetylglucosamines, in contrast to mannose phosphate in *S. cerevisiae* (Raschke and Ballou, 1972). In vaccinations, this could have considerable effects on the stimulation of the immune system by the respective yeast species.

The improved secretion of recombinant proteins in *K. lactis* mutants with modified α-1,6-mannosyl transferase (KlOCH1) clearly shows the connection between protein glycosylation/secretion and cell wall biosynthesis (Uccelletti et al., 2004). Moreover, changes in the protein glycosylation influence the intracellular localization of recombinant proteins which are held back on the path to secretion owing to incorrect folding.

*K. lactis* is one of the few yeast species which can utilize lactose as carbon and energy source. Lactose is a cheap sugar which arises in large quantities as a component of whey (e.g. as a by-product in the dairy industry). *K. lactis* can achieve similar growth rates with lactose as with glucose. The regulation of the genes involved in the lactose metabolism has been intensively studied. The strong β-galactosidase promoter (LAC4) can be utilized for regulation of the expression of heterologous genes and production of recombinant proteins (van Ooyen et al., 2006, Breunig et al., 2000). Owing to the decreased glucose repression, the heterologous expression of genes in *K. lactis* cultures which are cultured in glucose-containing media can be rapidly and efficiently induced by the addition of lactose.

According to the invention, a *K. lactis* strain, preferably VAK367-D4 and variants of this strain, which allows the targeted integration of foreign genes at the LAC4 locus of the yeast genome was generated by genetic engineering methods (FIG. 1). This integration requires only one step via an appropriately constructed plasmid; selection of recombinant strains is possible without the use of antibiotic resistance genes, and the foreign gene expression in the recombinant strains can be induced via the LAC4 promoter by the addition of lactose to the medium. *K. lactis* with integrated foreign genes can be generated and characterized in a few weeks via this method. Both aspects of this system are of great importance: firstly, reproducible growing of yeast cells which in each case contain defined quantities of a foreign protein is thus possible (FIGS. 2 & 3). Secondly, in case of use for vaccination against readily variable antigens (such as for example the influenza antigen hemagglutinin), new yeast strains can be generated in a short time, for example on emergence of new, potentially pandemic influenza virus strains. Further, there is high probability that the newly generated recombinant *K. lactis* strains will have similar properties to the proven strains (e.g. regarding their growth behavior in the fermenter). Further, through the additional integration of genes of the KlGal4 transactivator into the yeast genome, the expression rate of the foreign gene can be significantly increased (Kuger et al., 1990).

In a further embodiment, the method according to the invention is performed with a special *K. lactis* strain, VAK367-D4 and derivatives thereof. A series (VAK) of recombinant variants based on the *K. lactis* strain VAK367-D4 was generated. In general, these variants inducibly express significant quantities of a foreign protein, or domains of this foreign protein, or domains of this foreign protein fused with protein domains foreign to the species. The foreign protein domains used therein serve for specific stimulation of the immune response (adjuvant) or specific compartmentalization of the expressed protein in the yeast cell.

Together with adjuvant effects, compartmentalization of the expressed foreign protein is important for optimization of expression and formulation of the expression product.

In a further embodiment, the method according to the invention is performed with VAK367-D4 and derivatives thereof in the application as subunit marker vaccine. The use of recombinant *K. lactis* which express only defined protein antigens (foreign proteins) as a vaccine in a differential diagnosis allows the discrimination of vaccinated individuals from those naturally infected. One of these recombinant *K. lactis* strains (see practical examples) was successfully used for oral and subcutaneous vaccination. With subcutaneous administration, complete protection of the vaccinated individuals was obtained.

In the sense of this invention, “foreign proteins” means all proteins, polypeptides and proteins which are suitable for creating a protective immune response, preferably a protective humoral immune response, in man or in an animal against a pathogen or carcinogenically degenerated cells. Foreign proteins can derive from pathogens or tumors of any kind for which antigens have been characterized, which are capable alone of inducing a protective immune response, preferably a protective humoral immune response.

In a preferred embodiment, the foreign proteins derive from pathogens (viruses, bacteria or parasites) for which antigens have been characterized, which are capable alone of inducing a protective immune response, preferably a protective humoral immune response. These are for example:

Foreign Proteins which Derive from Parasites

*Necator americanus, Ancylostoma duodenale*: ASP protein, hemoglobin-degrading proteases

*Leishmania*: gp63, 46 kD promastigote antigen, LACK

*Plasmodium*: CSP protein, CSA-1, CSA-3, EXP1, SSP2, STARP, SALSA, MSP1, MSP2, MSPS, AMA-1, GLURP, Pfs25, Pfs 28, Pvs25, Pvs 28, Pfs 48/45, Pfs 230

*Schistosoma*: TP1, Sm23, ShGSTs 26 and 28, paramyosin, parasite myosin, Sm14

Foreign Proteins which Derive from Bacteria

*Mycobacterium tuberculosis*: Ag85A, Hsp65, R8307, 19 kD, 45 kD, 10.4

*Heliobacter pylori*: VacA, LagA, NAP, hsp, urease, catalase

Group A *Strepptococcus*: M, SCPA peptidase, exotoxins SPEA and SPEC, fibronectin binding protein

*Streptococcus pneumoniae*: PspA, Psa A, BHV 3, BHV 4

*Salmonella typhimurium*: Vi antigen

*Shigella*: LPS

*Vibrio cholerae*: CTB

*Escherichia coli* ETEC: LT, LT-ST, CTB

*Yersinia pestis*: Fl, V

Foreign Proteins which Derive from Tumor Cells/Tumors (Tumor-Associated Antigens, TAA)

CEA

5T4

MUC1

MART1

HER-2

Particularly Preferred are Foreign Proteins which Derive from Viruses

Calciviridae (Norwalk, HEV): NV 60 kD, HEV ORF2

Reoviridae (Rota): VP7, VP4

Retroviridae (HIV): Gag, Pol, Nef, Env, gp160, gp120, gp140, gp41

Flaviviridae (genus Flavivirus: WNV, dengue, YF, TBE, JEV): preM-Env, NS3, NS4, NS5

Flaviviridae (genus Pestivirus BVDV, CSFV, BDV, genus Hepacivirus HCV): E1, E2, $E^{RNA}$ (Pesti), C, NS3, NS4, NS5

Hepadnaviridae (HBV): HBS antigen

Paramyxoviridae (Paramyxovirinae: PIV-1, PIV-2, mumps,

Sendai, PIV-2, PIV-4, morbilli): M, HN, N, F

Paramyxoviridae (Pneumovirinae: RSV): F, G, SH, M

Rhabdoviridae (rabies): G

Herpesviridae (EBV, HSV2): gp350/220 (EBV), gB2, gD2 (HSV)

Coronaviridae (SARS): CoV, N, M, S

Orthomyxoviridae (influenza A, B): HA, NA, M1, M2, MP

Papillomaviridae: L2, E6, E7

In the most preferred embodiment of the invention, the foreign proteins derive from members of the family Birnaviridae, such as for example the IBD virus, and are capable of inducing a protective immune response, preferably a protective humoral immune response. In a preferred embodiment of the invention, a *K. lactis* VAK367-D4 variant VP2 (VAK887) was created which as a foreign protein expresses the capsid-forming VP2 antigen of the infectious bursitis virus (IBDV strain D78) (SEQ ID Nos.: 1 and 2). Particularly preferred is a *K. lactis* VAK367-D4 variant VP2-T2S (VAK888) in which the VP2 protein has been mutated at amino acid position 2 (replacement of threonine by serine; Jagadish et al. (1991)) and which has the nucleotide and amino acid sequence according to SEQ ID No.3 and 4 respectively.

In a particularly preferred embodiment of the invention, an optimized *K. lactis* VAK367-D4 variant, VP2T2S_GAL4 was created, in which the VP2 protein was mutated at amino acid position 2 (SEQ ID No.3 and 4) and which additionally contained at least two KIGAL4 genes (VAK890). Particularly preferred is a *K. lactis* VAK367-D4 variant, oVP2-T2S, in which the mutated VP2 antigen is encoded by the yeast codon-optimized nucleotide acid sequence with the SEQ ID No.5 and has the amino acid sequence according to SEQ ID No.6 in the recombinantly expressed VP2 antigen. The optimized *K. lactis* oVP2-T2S_GAL4 variant (VAK911) has the following advantages:

- the foreign protein is additionally stabilized by the mutation.
- a marked increase in VP2 expression could be achieved through the overexpression of the transactivator and/or by codon optimization of the sequence (FIG. 2).
- the integration of additional KIGAL4 genes also correlated with a higher growth rate of this *K. lactis* variant.
- this *K. lactis* exhibits particularly high reproducibility in high cell density fermentation and the quantity of expressed VP2 protein (FIG. 3).

The *K. lactis* VP2-T2S_GAL4 variant created according to the invention which as foreign protein recombinantly expresses the mutated VP2 antigen of IBDV and contains further copies of the KIGAL4 transactivator gene (VAK890) was deposited on 29 Nov. 2011 at the German Collection of Microorganisms and Cell Cultures GmbH, DSMZ, Inhoffenstrasse 7B, 38124 Braunschweig, Germany in accordance with the Budapest Treaty under the number DSM 25405.

The *K. lactis* oVP2-T2S variant created according to the invention which as foreign protein recombinantly expresses the mutated and codon-optimized VP2 antigen of IBDV (VAK910) was deposited on 29 Nov. 2011 at the German Collection of Microorganisms and Cell Cultures GmbH, DSMZ, Inhoffenstrasse 7B, 38124 Braunschweig, Germany in accordance with the Budapest Treaty under the number DSM 25406.

The *K. lactis* oVP2-T2S variant created according to the invention which as foreign protein recombinantly expresses the mutated and codon-optimized VP2 antigen of IBDV and contains further copies of the KIGAL4 transactivator gene (VAK911) was deposited on 29 Nov. 2011 at the German Collection of Microorganisms and Cell Cultures GmbH, DSMZ, Inhoffenstrasse 7B, 38124 Braunschweig, Germany in accordance with the Budapest Treaty under the number DSM 25407.

A further embodiment relates to use of the recombinant yeasts according to the invention in a method for the creation of a protective immunization, in particular a protective humoral immunization.

Such a method comprises the following steps:

a) growth and proliferation of the recombinant yeasts according to the invention,
b) harvesting and inactivation of the yeasts,
c) administration of the recombinant yeasts according to an immunization scheme to be specified,
d) titer determination of the antibodies formed and/or
e) detection of the immunization.

The growth and proliferation of the recombinant yeasts according to the invention can be performed with any conventionally available method. Particularly preferred here are methods which inexpensively result in high cell yields. These include fermentation methods, in particular high cell density fermentation methods. It has been found particularly advantageous to perform the fermentation using a fed batch fermentation protocol.

In a preferred embodiment, the protective, humoral immunization is achieved by administering the recombinant yeast orally/mucosally or subcutaneously. In a particularly preferred embodiment of the invention, the recombinant yeasts are administered subcutaneously. Particularly preferred in the method according to the invention is the use of *K. lactis*, especially the genetically modified variants VAK367-D4 and the variant VAK890 derived therefrom and variants thereof for subcutaneous administration.

The recombinant yeast cells should be used in the method according to the invention inactivated/killed. For this, after growth and expression of the foreign genes the yeasts are dried and then inactivated. The inactivation can be effected with any conventionally available method. Particularly suitable for use in the method according to the invention is heat inactivation (e.g. heat inactivation for 2 hours at 90° C.)

For the oral/mucosal vaccination, for example a short 1/1/1/1 immunization scheme (1 week feed, 1 week pause, 1 week feed, etc.) or a longer 2/2/2 scheme (2 weeks feed, 2 weeks pause, 2 weeks feed, etc.) can be used. For the subcutaneous vaccination, for example a double or triple administration at intervals of two weeks each time can be used (FIGS. 4 and 5).

For detection of the immunization effected, all conventional methods are available. In one embodiment of the invention, for the detection of the immunization the titer of virus-neutralizing antibodies is tested. For this, for example specific ELISA tests or neutralization assays can be performed. In the neutralization assay, a defined number of IBD viruses is treated with a defined volume of serum of an immunized animal or a control animal. Next inhibition of the infection (neutralization) by the viruses thus treated is tested for in cell culture. It is also possible to check whether an immunization was successful in a "challenge" experiment, for example in a "virus challenge" experiment. For this, a dose of a pathogenic micro-organism or virus which would normally lead to the disease in non-immunized animals is administered to the treated animals. If the animals do not become diseased after such a challenge, successful immunization has been demonstrated (FIG. 5). Finally, the immunization can also be detected by immunohistochemistry. For this, after the challenge, the pathogen's target organs are examined for infection or lesion (FIG. 5).

According to the invention, it was shown that recombinant *K. lactis* variants which were each derived from VAK367-D4 could successfully be used for vaccination by subcutaneous administration. The strain variant VAK890 described in the practical examples expresses the VP2 antigen of the infectious bursitis virus (IBDV: strain D78). The IBDV VP2 is a viral capsid-forming protein. It is known of VP2 that triggering of a humoral immune response to this antigen is sufficient to protect an infected organism preventively against a subsequent infection by the virus concerned (IBDV). Triggering of an effective humoral immune response could on the one hand be indexed by the quantification of virus-neutralizing antibodies. On the other hand, detection of a protective immune response was performed via a "virus challenge experiment" and immunohistochemistry after the virus challenge. Thus it was possible according to the invention to establish recombinant *K. lactis*, or recombinant *K. lactis* based on the strain VAK367-D4, in subcutaneous applications as an effectively acting, i.e. 90-100% protective, vaccine (90-100% corresponds to "gold standard" in vaccination) (FIGS. 4 and 5). The recombinant *K. lactis*, or recombinant *K. lactis* based on the strain VAK367-D4, was thereby established as a subunit marker vaccine against pathogens such as for example viruses. This means that a single, immunogenic protein subunit of a virus was used as the antigen. The use as "subunit" marker vaccine implies that its use enables the differentiation of vaccinated organisms from non-vaccinated, infected ones. This is for example possible by a differential diagnosis method which detects antibodies against the antigen used for the vaccination, as well as antibodies against a further antigen of the infectious pathogen. Through the immunization with the recombinant *K. lactis* strain VAK890 (DSM 25405), starting from the strain VAK367-D4, it was possible to create high antibody titers against the corresponding viral antigen. For these antibodies, it could be shown that they are virus-neutralizing. It can already be empirically deduced from this property and the measured high titer that this humoral immune response is sufficient to protect an organism against a subsequent infection with the virus concerned. The final proof could be obtained for IBDV. In the chicken model, the high titer of virus-neutralizing antibodies created correlated with complete protection of the vaccinated animals against a subsequent virus infection (FIG. 5).

The use of *K. lactis*, especially of a genetically modified variant, VAK367-D4 and derivatives thereof, such as for example *K. lactis* VP2-T2S_GAL4 (VAK890) has the following significant advantages compared to conventional methods:

1. For use for foreign gene expression, *K. lactis* has significant, fundamental advantages compared to *S. cerevisiae*, which are based on the physiology of *K. lactis* diverging from *S. cerevisiae* over millions of years.
2. The expression of the foreign gene does not occur via plasmid vectors but after targeted and stable integration of the foreign gene into a defined gene locus of the *K. lactis* genome. This allows high reproducibility of the protein expression under non-selective conditions. This aspect is essential for the reproducible creation of the vaccine by culturing of the yeast strain in the fermenter. The principle of the strain VAK367-D4 and derivatives thereof has already been described for an oral vaccination (WO 20101054649 A2). In the present invention, it is now shown that the strain VAK367-D4 and derivatives thereof, in particular *K. lactis* VP2-T2S_GAL4 (VAK890) and oVP2-T2S_GAL4 (VAK911) in subcutaneous vaccination with use of considerably smaller quantities of yeast results in effective protection in virus infections.
3. The gene expression is inducible and can be further increased by increasing the concentration of the transcription activator Gal4 and/or by codon optimization of the nucleotide sequence of the foreign gene to match the yeast host. The establishment of a fed batch fermentation protocol allows efficient production even of cytotoxic antigens.
4. The integration of the foreign gene into VAK367-D4 and derivatives thereof is a "one-step procedure". This means that in ca. 3 weeks new recombinant strains can be created and characterized; this is particularly important for the rapid development of efficient vaccines against modified virus variants.
5. Through subcutaneous administration of recombinant yeast of the *K. lactis* type, especially recombinant yeast of the strain VAK367-D4 and derivatives thereof, a protective immune response could be created both in the mouse and also in the chicken. The procedure is extremely simple: a defined quantity of inactivated (heat-killed) yeast cells is injected into the vaccinated animal under the skin in a 2-3 fold procedure. Two weeks after the last application, the serum of the vaccinated animal is tested for the presence and functionality of antigen-specific antibodies. By virus neutralization tests, it could be shown that this immune response was based predominantly if not exclusively on the creation of neutralizing antibodies (protective humoral immune response). Hence the immune response inducible by *K. lactis* in subcutaneous application differs fundamentally from the immune response inducible by *S. cerevisiae*, which mainly induces a T cell response. Hence the possibilities for subcutaneous use of *K. lactis* are fundamentally different from the possibilities for subcutaneous use of *S. cerevisiae*: while *K. lactis* can be used as a subunit vaccine in case of antigens which can create a protective humoral immune response (e.g. viral antigens such as the VP2 antigen of the infectious bursitis virus, IBDV, or hemagglutinin HA antigen of the influenza virus), then *S. cerevisiae* can be used as a subunit vaccine in case of antigens which can create a protective cellular immune response (such as for example with the NS3 protein of the hepatitis C virus or tumor antigens such as Her-2). These differences in the form of the induced immune response are presumably attributable to the greatly different properties of the *S. cerevisiae* and *K. lactis* cells which were described above.

In summary, the present invention makes an extensive contribution to the state of the art and provides many advantageous embodiments compared to the prior art:

- the inventors have succeeded in producing subunit marker vaccines with which it is possible to distinguish vaccinated individuals from naturally infected ones.
- furthermore, subunit marker vaccines can be produced which simultaneously have strong adjuvant properties and hence are strongly immunogenic.
- the subunit marker vaccines according to the invention can be applied repeatedly.
- the subunit marker vaccines according to the invention create a systemic protective immune response and immunological memory in the vaccinated animal.
- with the present invention it is also possible to produce vaccines against cytotoxic antigens.
- the method according to the invention enables the fastest possible creation of new vaccine variants.
- the vaccination methods are in particular very inexpensive.
- for the production of the vaccines according to the invention no experimental animals nor the use of animal or human cells in culture are necessary.
- the vaccines according to the invention are not temperature-sensitive, they can be transported and stored without refrigeration.
- in the method according to the invention, no live recombinant cells or organisms are used.
- with the method according to the invention, it is possible to restrict both the quantities of vaccine used and also the number of applications which are necessary for achieving a protective immunization to a minimal level.

PRACTICAL EXAMPLES

1. Creation of the *K. lactis* Strain VAK367-D4 (metA ura3-5 lac4::ScURA3).

The starting strain VAK367 for heterologous expression of foreign proteins has the following properties: it allows culturing at high density, without intracellular proteins being detectably released in the process. In this respect, this strain differs from many closely related *K. lactis* strains. The strain VAK367 was derived from the strain CBS 2359 (Centraalbureau voor Schimmelcultures www.fungaibiodiversitycentre, com) by two rounds of mutagenesis and is auxotrophic for the amino acid methionine and the nucleobase uracil. The strain VAK367-D4 (deposited on 18 Nov. 2009 at the German Collection of Microorganisms and Cell. Cultures GmbH (DSMZ) in Braunschweig under the deposition number DSM 23097) was derived from the strain VAK367 by genetic engineering methods, by replacing the sequence+358 to +1181 of the LAC4 gene by the ScURA3 gene by means of the plasmid pD4-2. The strain VAK367-D4 now allows the integration of foreign genes at the LAC4 locus without additional markers since lactose growth is selected for. At the same time, with use of a suitable integration vector, such as for example KIp3-MCS (FIG. 6) the disruption cassette is replaced by homologous recombination such that an intact LAC4 gene is reconstituted with loss of the ScURA3 marker (FIG. 1).

2. Creation of an Integration Vector which Allows the Inducible Expression of Foreign Genes.

Vector: KIp3-MCS (SEQ ID No.10)

The vector KIp3-MCS (SEQ ID No.10) (FIG. 6) is an *E. coli* vector based on YRp7 which cannot replicate autonomously in yeasts since the ARS1 sequence has been deleted. KIp3-MCS (SEQ ID No.10) contains the *K. lactis* LAC4 promoter and sequences which enable integration at the LAC4 locus by homologous recombination.

Between LAC4 promoter and transcription start, a DNA segment which contains the TEF1 terminator and the KIGAL80 promoter were inserted. As a result, the LAC4 reading frame after reconstitution via homologous recombination can be expressed under the control of the KIGAL80 promoter. The KIGAL80 promoter is co-regulated with the LAC4 promoter via the transcription factor KIGa14 (Zenke et al., 1993). This construct makes it possible to monitor the induction of foreign gene expression via measurement of the LAC4-encoded β-galactosidase. KIp3-MCS (SEQ ID No.10) allows the insertion of the foreign gene between LAC4 promoter and TEF1 terminator via one of the unique cleavage sites in the multiple cloning site (MCS) (FIG. 6). For the integration, the resulting plasmid is digested with suitable restriction enzymes, so that the expression cassette is separated from the *E. coli* vector sequences. After transformation into *K. lactis* VAK367-D4, the expression cassette is chromosomally integrated; the resulting strains contain no bacterial sequences.

3. *K. lactis* Variant which Expresses the VP2 Antigen of the Infectious Bursitis Virus (IBDV Variant D78).

Production of the recombinant yeast strain The cDNA which codes for IBDV D78 VP2 was amplified from the plasmid pD78A (Icard et al., 2008) by means of the following oligonucleotides:

IBDV_AscI_fwd (5'-GGCGCGCC-GATGACAAACCTGCAAGATC-3') (SEQ ID No.7), containing an AscI restriction site, and VP2_NotI_rev (5'-ATAAGAATGCGGCCGCTCACACAGCTATCCTCCT-TAT G-3') (SEQ ID No.8), containing a NotI restriction site.

For the generation of VP2-T2S, the following oligonucleotide pair was used:

IBDV_S:T_AscI_fwd (5'-GGCGCGCC-GATGTCTAACCTGCAAGATCAAA CCCA-3') (SEQ ID No.9) and VP2_NotI_rev (see above).

After checking and confirmation of the nucleotide sequences, the DNA fragments thus amplified were cloned into the vector KIp3-MCS (SEQ ID No.10) (FIG. 6) via the AscI and NotI cleavage sites. After this, the integration into the genome was effected (FIG. 1). In detail, the integration plasmid was digested with the restriction enzyme EcoRI and the digested fragments transformed into competent VAK367-D4 cells. The transformed cells were plated onto YEPD medium and incubated overnight at 30° C. For detection of positive colonies, the transformation plate was duplicated onto SM medium which contained lactose as the carbon source and incubated for 2 days at 30° C. The positive clones identified by this method were further investigated.

The genomic integration of additional KIGAL4 gene copies was effected by a conventional method (Kuger et al. (1990)). The codon optimization followed a *Saccharomyces cerevisiae* algorithm (mr.gene.com, Raab et al., 2010). The codon-optimized DNA fragments were synthesized directly. In the synthesis, the 5' AscI and 3' NotI restriction sites were already incorporated (mr.gene.com, Regensburg, Germany). Cloning into the vector KIp3-MCS (SEQ ID No.10) was then effected. XXXXXXXXXXXXXX-XXXXXXXXXXXXXXXXXXXXXXXXXXXXX Western Blot Analysis Cell pellets were resuspended in B60 buffer (50 mM HEPES-KOH pH 7.3; 60 mM potassium acetate, 5 mM magnesium acetate, 0.1% Triton X100, 10% glycerol, 1 mM sodium fluoride, 20 mM glycerol phosphate, 10 mM $MgCl_2$, 1 mM DTT, protease complete inhibitor (Roche)) and lysed by vigorous mixing with glass beads. The extract was centrifuged (14,000 rpm, 20 mins at 4° C.) and the protein concentration determined. 40 μg of the protein extract were separated by SDS-PAGE in a 12% gel. The proteins were then transferred onto a membrane. The Western blot analyses were performed with an α-IBDV antiserum from rabbits (1:15,000, Granzow et al., 1997) and a goat-anti-rabbit HRP-coupled antibody (1:3,000, Santa Cruz Biotechnology Inc.) using conventional methods.

Northern Blot Analysis

For the complete extraction of the RNA, 5 ml of a yeast culture were cooled on ice. The cell lysis was performed in Proteinase K buffer (100 mM Tris/HCl pH 7.9, 150 mM NaCl, 25 mM EDTA, 1% SDS) and 50 mg proteinase K (Fermentas) with vigorous shaking with glass beads. The samples were incubated for 1 hr at 35° C. and the RNA extracted, precipitated with ethanol and resuspended in DEPC water. The Northern analysis was performed as described in Engler-Blum et al., 1993, but with some differences. 5 μg of the total RNA were separated on a 1% formaldehyde-agarose gel and transferred onto a nylon membrane (Amersham Hybond™-N+, GE Healthcare). The membrane was incubated at 68° C. with a DIG-labeled RNA probe which was produced by in vitro transcription of PCR fragments in the presence of DIG(Digoxigenin)-NTPs (Roche). The blot was treated with a blocking solution and incubated with an anti-DIG alkaline phosphatase-conjugated antibody (Roche). The determination of the activity of the alkaline phosphatase was determined by conventional methods.

Quantification of Heterologously Expressed VP2.

A modified protocol according to Saugar et al., 2005, was used. 2,000 ODU of a yeast culture which had been transformed with an episomal VP2 plasmid (pADH1-P_VP2-T2S) were cultured overnight on selective medium (0.67% YNB, 2% glucose and the following additions: 11 mg/l Ade, 14 mg/l Tyr, 38 mg/l each of His, Trp, Arg and Met, 48 mg/l Phe, and 58 mg/l each of Leu, Ile, Lys, Val and Thr). After harvesting and washing with distilled water, the cells were disintegrated with glass beads in lysis buffer (10 mM Tris (pH 8.0), 150 mM NaCl, 20 mM $CaCl_2$, 1 mM EDTA, protease complete inhibitor (Roche), pH 8.0). The resulting protein extract was centrifuged (10,000 g for 1 hr at 4° C.) and the soluble fraction layered onto a 20% (w/v) sucrose cushion in sucrose buffer (10 mM Tris pH 8.0, 150 mM NaCl, 20 mM $CaCl_2$, containing protease complete inhibitor (Roche)). After centrifugation at 170,000 g for 3 hrs at 4° C., the pellet was dissolved in 200 μl of sucrose buffer and centrifuged for a further 17 hrs at 114,000 g in a 20 to 53% sucrose gradient in sucrose buffer. The gradient was collected in 700 μl fractions and analyzed by SDS-PAGE and Western blot. Oligomeric protein complexes of the heterologously expressed VP2 could thus be concentrated and purified. The protein could be detected and the quantity of protein determined by SDS PAGE and Coomassie staining in comparison to a standard protein (not shown). The VP2 thus purified was then used as standard in a comparative Western blot with anti-VP2 antibodies. The VP2 content of a defined number of yeast cells from different fermentations was compared (FIG. 3).

Yeast Fermentation and Heat Inactivation.

All experimental fermentations were performed in a DasGip parallel bioreactor system (DasGip AG, Julich, Germany) with four fully equipped 2 l fermenters. Fermentations on the production scale were performed by Organobalance GmbH (Berlin, Germany) or in our own laboratory in a Biostat ED bioreactor (B. Braun Biotech, Melsungen, Germany) with 10 l working volume. All production processes were performed by the fed batch method. A complex culture medium containing 2% yeast extract and 1% peptone and a 20% lactose feed solution was utilized. The temperature of the yeast culture was maintained at 30° C. and the $pO_2$ was controlled at 30% saturation. The pH was maintained at 5.0 during the fermentation by addition of 2M NaOH or 2M $H_3PO_4$.

For the in vivo experiments in mice and chickens, the yeasts were freeze-dried and then heat-inactivated for 2 hrs at 90° C. By using this process, fewer than 10 cells per gram cell dry weight were viable.

4. Subcutaneous Administration in Mice

For the subcutaneous administration in mice of a *K. lactis* variant which expresses the VP2 antigen of the infectious bursitis virus (IBDV variant D78) (VAK890), the dried and pulverized yeast was mixed with complete Freund adjuvant (CFA) for the first application, and in the further applications the yeast was mixed with incomplete Freund adjuvant (IFA) (100 μg yeast material per 200 μl CFA or IFA). 200 μl of the emulsions (with 100 μg contained yeast) was injected per individual per immunization/boost. Thus the quantity of VP2 administered per subcutaneous administration to a single mouse corresponded to ca. 18 ng (FIG. 3). After the initial injection (day 0), this was "boosted" twice at two-week intervals (on day 14 and 28, FIG. 4). After a further two weeks, the animals were killed by narcosis to obtain the blood serum.

5. Subcutaneous Administration in Chickens

For subcutaneous administration in chickens, 5 mg of the dried and pulverized *K. lactis* variant which expresses the VP2 antigen of the infectious bursitis virus (IBDV variant D78) (VAK890) were dissolved in 750 μl of phosphate buffer/saline (PBS) and 500 μl distilled water and an emulsion with 1.25 ml of IFA prepared. 500 μl of this emulsion (with 1 mg contained yeast) were injected on day 0, 14 and day 28 (FIG. 5). Thus the quantity of VP2 administered per subcutaneous immunization of a single chicken corresponded to ca. 180 ng (FIGS. 3 & 4).

6. Virus "Challenge"

After the vaccination (FIG. 5), vaccinated chickens were infected on day 42 via the oral route with 100 $EID_{50}$ of the IBDV strain "Edgar" and the mortality rate determined after six days. The animals were then killed under narcosis, after which the sera were obtained and the animals' bursae removed. These were firstly fixed for 24 hours in 10% neutral buffered formalin and then embedded in paraffin wax.

7. Enzyme-Linked Immunosorbent Assay (ELISA).

The IBDV-specific antibody titers in the sera of the vaccinated animals were determined with a commercial ELISA test, IDEXX FlockCheck® IBD ELISA kit (IDEXX Laboratories, Inc.). In the case of the sera from vaccinated mice, a secondary antibody from a different manufacturer was used (Sigma Aldrich).

8. Neutralization Assay.

The neutralization assay for the determination of the concentration of virus-neutralizing antibodies was performed according to the protocol of Schröder et al., 2000.

9. Immunohistochemistry.

Organ sections 4 micrometers thick were prepared from the wax-embedded bursae. After removal of the wax, these were stained with hematoxylin and eosin by standard procedures. The samples were examined microscopically and the so-called "lesions score" on a scale of 1-4 determined (1=normal to 10% follicular atrophy, 2=10-30% follicular atrophy, 3=30-70% follicular atrophy and 4=>70% atrophy).

Results

Production and Quantification of the IBDV VP2-Expressing *K. lactis* Strain

Different *K. lactis* variants with integrated IBDV VP2 gene were prepared. For the vaccination experiments, an optimized variant was used in which the VP2 protein was mutated at amino acid position 2 (replacement of threonine by serine; Jagadish et al. (1991)), and which contained an additional tandem integration of at least two KIGAL4 genes (variant VP2-T2S_GAL4, strain VAK890). The foreign protein was additionally stabilized by the mutation; through the overexpression of the trans activator, a marked increase in VP2 expression could be achieved (FIG. 2). The integration of additional KIGAL4 genes also correlated with a higher growth rate of this *K. lactis* variant. The growth conditions for the particular VP2-expression *K. lactis* strain VAK890 were optimized so that the yeast could be fermented at high densities and with a reproducible quantity of expressed VP2. After production, the yeast was freeze-dried and inactivated for 2 hours at 90° C. The inactivation was confirmed: fewer than 10 living yeast cells remained per g of inactivated yeast material. The quantity of VP2 per yeast cell was determined: with the strain VAK890 it was ca. 0.7 fg of heterologous VP2 protein per yeast cell (FIG. 3).

Subcutaneous Administration in Mice and Chickens

The immunizations were performed as described above; two weeks after the last administration the sera of the treated vaccinated animals were tested for the presence of neutralizing antibodies. For this an IBDV-specific ELISA was used and an IBDV neutralization assay performed (FIGS. 4 and 5). In addition, with the vaccinated chickens a "virus challenge" experiment was performed. For this the animals were given a viral dose of 100 EID50 per animal of the strongly virulent IBDV strain "Edgar", a concentration which in non-vaccinated poultry results in significant bursitis with a mortality rate of ca. 10-35% in non-vaccinated poultry (FIG. 5D). Following the "virus challenge" experiment, the bursae of the vaccinated animals were examined by immunohistochemistry for signs of infection and lesions in the bursae and characterized by the so-called "lesions score" (FIG. 5).

Both the experiments with mice and also the experiments with chickens showed that through the subcutaneous administration of the *K. lactis* strain VAK890 high titers of virus-neutralizing antibodies could be created in practically all treated animals (FIGS. 4B & 4C and FIGS. 5B & 5C). Likewise, it could be shown that practically all vaccinated test chickens were protected against virus challenge and showed practically no signs of a viral infection in their bursae (FIG. 5). Hence all animals vaccinated with the *K. lactis* strain VAK890 showed a significant humoral immune response against VP2. This immune response could already be observed after a single boost, from which it can be concluded that two injections, which moreover were performed with incomplete Freund adjuvant (immunization and one boost), are already sufficient to produce protection. Further, all test chickens which were vaccinated with the *K. lactis* strain VAK890 were protected against a subsequent virus infection (FIG. 5).

ABBREVIATIONS

ARS1 autonomously replicating sequence: nucleotide sequence on the
DNA on which the replication is initiated
Asc I restriction endonuclease Asc I
CFA complete Freund adjuvant
DNA deoxyribonucleic acid
DEPC diethyl pyrocarbonate
DIG-NTP digoxigenin nucleotide triphosphate
DSMZ German Collection of Microorganisms and Cell Cultures GmbH
DTT dithiothreitol
*E. coli Escherichia coli*
EcoRI restriction endonuclease Eco RI
EDTA ethylenediaminetetraacetic acid
EID50 egg or embryo infectious dose—number of infectious viruses which is necessary to trigger an infection in 50% of infected eggs
ELISA enzyme-linked immunosorbent assay
GAL4 yeast-specific transcription activator
GRAS generally regarded as safe
HEPES 2-(4-(2-hydroxyethyl)-1-piperazinyl)-ethanesulfonic acid
Hpa I restriction endonuclease Hpa I
HRP horseradish peroxidase
IBDV infectious bursitis virus
IFA incomplete Freund adjuvant
*K. lactis Kluyveromyces lactis*
KIGAL4 *K. lactis* gene coding for the KIGal4/Lac9 protein
KIGAL80 *K. lactis* gene coding for the KIGal80 protein
LAC4 *K. lactis* gene coding for a β-galactosidase enzyme
Notl restriction endonuclease Not I
ODU optical density unit
PBS phosphate buffer/saline
PCR polymerase chain reaction
RNA ribonucleic acid
*S. cerevisiae Saccharomyces cerevisiae*
Sal I restriction endonuclease Sal I
SDS sodium dodecylsulfate
SDS-PAGE polyacrylamide gel electrophoresis using SDS
TEF1 Arxula adeninivorans gene coding for the translation factor EF-1 alpha
VP2 capsid-forming viral protein of IBDV
VP2-T2S VP2 with an amino acid replacement of threonine by serine at position 2
VAK vaccine strain
YEPD yeast extract peptone dextrose
YRp7 *S. cerevisiae-E. coli* shuttle vector, Genbank accession U03501 (Botstein et al., 1979)

LIST OF REFERENCES

Backhaus, K. et al. Milk and sugar: Regulation of cell wall synthesis in the milk yeast *Kluyveromyces lactis. European Journal of Cell Biology* 90, 745-750 (2011).

Bathurst, I C. Protein Expression in Yeast as an Approach to Production of Recombinant Malaria Antigens. *The American Journal of Tropical Medicine and Hygiene* 50, 20-26 (1994).

Botstein D, Falco, S C., Stewart, S E., Brennan, M., Scherer, S., Stinchcomb, D. T., Struhl, K. & Davis, R. W. Sterile host yeast (SHY): a eukaryotic system of biological containment for recombinant DNA experiments. *Gene* 8, 17-24 (1979).

Breunig et al. Regulation of primary carbon metabolism in *Kluyveromyces lactis. Enzyme Microbial Technology* 26, 771-780 (2000).

Chen, X. J. & Clark-Walker, G D. Specific mutations in alpha and gamma subunits of Fl-ATPase affect mitochondrial genome integrity in the petite-negative yeast *Kluyveromyces lactis. EMBO Journal* 14, 3277-3286 (1995).

Clark-Walker, G D. The Fl-ATPase inhibitor Inhl (IFl) affects suppression of mtDNA loss-lethality in *Kluyveromyces lactis. FEMS Yeast Research* 7, 665-674 (2007).

Donnini, C. et al. Improved Production of Heterologous Proteins by a Glucose Repression-Defective Mutant of *Kluyveromyces lactis. Applied and Environmental Microbiology* 70, 2632-2638 (2004).

Engler-Blum, G., Meier, M., Frank, J. & Muller, G A. Reduction of background problems in nonradioactive northern and southern blot analyses enables higher sensitivity than 32P-based hybridizations. *Analytical Biochemistry* 210, 235-244 (1993).

Cellissen G. & Hollenberg C P. Application of yeasts in gene expression studies: a comparison of *Saccharomyces cerevisiae, Hansenula polymorpha* and *Kluyveromyces lactis*—a review. *Gene* 190, 87-97 (1997).

Granzow, H. et al. A second form of infectious bursal disease virus-associated tubule contains VP4. *Journal of Virology* 71, 8879-8885 (1997).

Jagadish, M. N., Laughton, D. L., Azad, A. A. & Macreadie, I. G. Stable synthesis of viral protein 2 of infectious bursal disease virus in *Saccharomyces cerevisiae. Gene* 108, 275-279 (1991).

Icard, A. H., Sellers, H S., & Mundt, E. Detection of infectious bursal disease virus isolates with unknown antigenic properties by reverse genetics. *Avian Disease* 52, 590-598. (2008)

Kuger, P., Godecke, A. & Breunig, K. D. A mutation in the Zn-finger of the GAL4 homolog LAC9 results in glucose repression of its target genes. *Nucleic Acids Research* 18, 745-751 (1990).

Lu, Y. et al. Mutation-Selective Tumor Remission with Ras-Targeted, Whole Yeast-Based Immunotherapy. *Cancer Research* 64, 5084-5088 (2004).

Raab, D., Graf, M., Notka, F., Schadl, T. & Wagner, R. The GeneOptimizer Algorithm: using a sliding window approach to cope with the vast sequence space in multiparameter DNA sequence optimization. *Systems and Synthetic Biology* 4, 215-225 (2010).

Raschke, W. C. & Ballou, C E. Characterization of a yeast mannan containing N-acetyl-D-glucosamine as an immunochemical determinant. *Biochemistry* 11, 3807-3816 (1972).

Saugar, I. et al. Structural polymorphism of the major capsid protein of a double-stranded RNA virus: An Amphipathic [alpha] Helix as a Molecular Switch. *Structure* 13, 1007-1017 (2005).

Schröder, A., van Loon, A. A. W. M., Goovaerts, D. & Mundt, E. Chimeras in noncoding regions between serotypes I and II of segment A of infectious bursal disease virus are viable and show pathogenic phenotype in chickens. *Journal of General Virology* 81, 533-540 (2000).

Stubbs, A C. et al. Whole recombinant yeast vaccine activates dendritic cells and elicits protective cell-mediated immunity. *Nature Medicine* 7, 625-629 (2001).

Stubbs, A C. & Wilson, C. C. Recombinant yeast as a vaccine vector for the induction of cytotoxic T-lymphocyte responses. *Current Opinion of Molecular Therapy* 4, 35-40 (2002)

Uccelletti, D., Farina, F., Mancini, P. & Palleschi, C. KIPMR1 inactivation and calcium addition enhance secretion of non-hyperglycosylated heterologous proteins in *Kluyveromyces lactis. Journal of Biotechnology* 109 93-101 (2004).

Van Ooyen, A. J., Dekker, P., Huang, M., Olsthoorn, M. M., Jacobs, D. I., Colussi, P A. & Taron, C H. Heterologous protein production in the yeast *Kluyveromyces lactis. FEMS Yeast Research* 6, 381-392 (2006).

Wansley E. K. et al. Vaccination with a recombinant *Saccharomyces cerevisiae* expressing a tumor antigen breaks immune tolerance and elicits therapeutic antitumor responses. *Clinical Cancer Research* 14, 4316-4325 (2008).

Zenke, F T., Zachariae, W., Lunkes, A., & Breunig, K. D. Gal8O proteins of *Kluyveromyces lactis* and *Saccharomyces cerevisiae* are highly conserved but contribute differently to glucose repression of the galactose regulon. *Molecular and Cellular Biology* 13, 7566-7576 (1993)

The invention claimed is:

1. A recombinant yeast of the species *Kluyveromyces lactis,* said recombinant yeast comprising a genomically integrated expression cassette comprising lactose inducible LAC4 promoter from *Kluyveromyces lactis*, a foreign gene or a part of a foreign gene, a transcription terminator and GAL80 promoter from *K lactis* (KIGAL80-P) which drives transcription of a LAC4 coding sequence, wherein the foreign gene or the part of the foreign gene is flanked by the lactose inducible LAC4 promoter and the transcription terminator, which transcription terminator is followed downstream by the KIGAL80-P;

and wherein the foreign gene is expressed as a foreign protein, and wherein subcutaneous administration of the recombinant yeast creates a protective humoral immune response.

2. The recombinant yeast as claimed in claim 1, wherein integration of the foreign gene was effected without additional vector sequences or selection markers.

3. The recombinant yeast as claimed in claim 1, wherein the foreign gene expression takes place constitutively.

4. The recombinant yeast as claimed claim 1, wherein the foreign gene expression is inducible.

5. The recombinant yeast as claimed in claim 1, wherein the foreign gene expression can be indirectly quantified via the expression of an endogenous reporter gene.

6. The recombinant yeast as claimed in claim 1, wherein the foreign gene enables the expression of a foreign protein with antigenic properties.

7. The recombinant yeast as claimed in claim 1, wherein the recombinant yeast inducibly or constitutively expresses significant quantities of a foreign protein or domains of this foreign protein or domains of this foreign protein fused with protein domains foreign to the species.

8. The recombinant yeast as claimed in claim 1, wherein the *Kluyveromyces lactis* strain is *Kluyveromyces lactis* VAK367-D4 (DSM 23097).

9. The recombinant yeast as claimed in claim 1, wherein the foreign protein derives from a pathogen or a tumor.

10. The recombinant yeast as claimed in claim 9, wherein the foreign protein is a tumor-associated antigen selected from CEA, 5T4, MUC1, MART1 and HER-2.

11. The recombinant yeast as claimed in claim 9, wherein the foreign protein derives from a virus, a bacterium or a parasite.

12. The recombinant yeast as claimed in claim 11, wherein the foreign protein derives from a parasite.

13. The recombinant yeast as claimed in claim 12, wherein the foreign protein derives from *Necator americanus, Ancylostoma duodenale, Leishmania spec., Plasmodium spec.* or *Schistostoma spec.*

14. The recombinant yeast as claimed in claim 12, wherein the foreign protein is selected from the group comprising:

*Necator americanus* or *Ancylostoma duodenale*: ASP protein and hemoglobin-degrading proteases;

*Leishmania spec.*: gp63, 46 kD promastigote antigen, LACK;

*Plasmodium spec.*: CSP protein, CSA-1, CSA-3, EXP1, SSP2, STARP, SALSA, MSP1, MSP2, MSP3, AMA-1, GLURP, Pfs25, Pfs 28, Pvs25, Pvs 28, Pfs 48/45, Pfs 230;

*Schistosoma spec.*: TP1, Sm23, ShGSTs 26 and 28, paramyosin, parasite myosin, Sm14.

15. The recombinant yeast as claimed in claim 11, wherein the foreign protein derives from a bacterium.

16. The recombinant yeast as claimed in claim 15, wherein the foreign protein derives from *Mycobacterium tuberculosis, Heliobacter pylori*, group A *Streptococcus* spec., *Streptococcus pneumoniae, Salmonella typhimurium, Shigella spec., Vibrio cholerae, Escherichia coli* or *Yersinia pestis.*

17. The recombinant yeast as claimed in claim 15, wherein the foreign protein is selected from the group consisting of:

*Mycobacterium tuberculosis*: Ag85A, Hsp65, R8307, 19 kD, 45 kD, 10.4;

*Heliobacter pylori*: VacA, LagA, NAP, hsp, urease, catalase;

Group A *Streptococcus spec.*: M, SCPA peptidase, exotoxins SPEA and SPEC, fibronectin binding protein;

*Streptococcus pneumoniae*: PspA, Psa A, BHV 3, BHV 4;

*Salmonella typhimurium*: Vi antigen;

*Shigella spec.*: LPS;

*Vibrio cholerae* CTB;

*Escherichia coli*: ETEC: LT, LT-ST, CTB; and

*Yersinia pestis*: F1 and V.

18. The recombinant yeast as claimed in claim 11, wherein the foreign protein derives from a virus.

19. The recombinant yeast as claimed in claim 18, wherein the foreign gene enables the expression of a viral protein with antigenic properties.

20. The recombinant yeast as claimed in claim 19, wherein the foreign gene enables the expression of a viral structural protein.

21. The recombinant yeast as claimed in claim 20, wherein the foreign protein derives from the Birnaviridae, Caliciviridae, Reoviridae, Retroviridae, Flaviviridae, Hepadnaviridae, Paramyxoviridae, Rhabdoviridae, Herpesviridae, Coronaviridae, Orthomyxoviridae or Papillomaviridae.

22. The recombinant yeast as claimed in claim 21, wherein the foreign protein is selected from the group consisting of:

Birnaviridae: VP2

Caliciviridae (Norwalk, HEV): NV 60 kD, HEV ORF2;

Reoviridae (Rota): VP7, VP4;

Retroviridae (HIV): Gag, Pol, Nef, Env, gp160, gp120, gp140, gp41;

Flaviviridae (genus Flavivirus: WNV, dengue, YF, TBE, JEV): preM-Env, NS3, NS4, NS5;

Flaviviridae (genus Pestivirus BVDV, CSSFV, BDV, genus Hepacivirus HCV): E1, E2, ERNA (pesti), C, NS3, NS4, NS5;

Hepadnaviridae (HBV): HBS antigen;

Paramyxoviridae (Paramyxovirinae: PIV-1, PIV-2, mumps, Sendai, PIV-2, PIV-4 morbilli): M, HN, N, F;

Paramyxoviridae (Pneumovirinae: RSV): F, G, SH, M;

Rhabdoviridae (rabies): G;

Herpesviridae (EBV, HSV2): gp350/220 (EBV), gB2, gD2 (HSV);

Coronaviridae (SARS): CoV, N, M, S;

Orthomyxoviridae (influenza A, B): HA, NA, M1, M2, NP; and

Papillomaviridae: L2, E6, E7.

23. The recombinant yeast as claimed in claim 18, wherein the foreign protein derives from a member of the family Birnaviridae.

24. The recombinant yeast as claimed in claim 18, wherein the foreign protein is VP2 antigen of infectious bursitis virus (IBDV).

25. The recombinant yeast as claimed in claim 24, wherein the VP2 antigen derives from infectious bursitis virus (IBDV) strain D78.

26. The recombinant yeast as claimed in claim 25, wherein the VP2 antigen of the infectious bursitis virus (IBDV) is encoded by a nucleotide sequence selected from SEQ ID No.1, SEQ ID No.3 and SEQ ID No.5.

27. The recombinant yeast as claimed in claim 26, wherein the VP2 antigen of the infectious bursitis virus (IBDV) has an amino acid sequence selected from SEQ ID No.2, SEQ ID No.4 and SEQ ID No.6.

28. The recombinant yeast as claimed in claim 1, wherein the

*Kluyveromyces lactis* is a strain selected from;

*Kluyveromyces lactis* VAK367-D4 890 DSM 25405,

*Kluyveromyces lactis* VAK367-D4 910 DSM 25406, and

*Kluyveromyces lactis* VAK367-D4 911 DSM 25407.

29. The recombinant yeast as claimed in claim 18, wherein the foreign protein is a mutated V antigen of infectious bursitis virus (IBDV).

30. The recombinant yeast as claimed in claim 18, wherein the foreign protein is a codon-optimized VP2 antigen of infectious bursitis virus (IBDV).

31. The recombinant yeast as claimed in claim 1, wherein the *Kluyveromyces lactis* is a strain selected from *Kluyveromyces lactis* VAK890, VAK910 and VAK911.

32. A method for subcutaneous vaccination by means of recombinant yeast, comprising the following steps:

a) growing and proliferating the recombinant yeast of the species *Kluyveromyces lactis,* b) harvesting and inactivating the yeast, c) administering the recombinant yeast according to a predetermined subcutaneous immunization scheme, d) titer determination of antibodies formed by the administration of the recombinant yeast and/or e) detection of the immunization;

wherein said recombinant yeast comprises a generically integrated expression cassette comprising lactose inducible LAC4 promoter from *Kluyveromyces lactis*, a foreign gene or a part of a foreign gene, a transcription terminator and GAL80 promoter from *K. lactis* (KI-GAL80-P) which drives transcription of a LAC4 coding sequence, wherein the foreign gene or the part of the foreign gene is flanked by the lactose inducible LAC4 promoter and the transcription terminator, which transcription terminator is followed downstream by the KIGAL80-P; and wherein the foreign gene is expressed as a foreign protein, and wherein administration of the recombinant yeast creates a protective humoral immune response.

33. A method for subcutaneous vaccination by means of a recombinant yeast, comprising subcutaneously administering a vaccine comprising a recombinant yeast of the species *Kluyveromyces lactis*, wherein said recombinant yeast comprises a genomically integrated expression cassette comprising lactose inducible LAC4 promoter from *Kluyveromyces lactis*, a foreign gene or a part of a foreign gene, a transcription terminator and GAL80 promoter from *K lactis* (KIGAL80-P) which drives transcription of a LAC4 coding sequence, wherein the foreign gene or the part of the foreign gene is flanked by the lactose inducible LAC4 promoter and the transcription terminator, which transcription terminator is followed downstream by the KIGAL80-P;

and wherein the foreign gene is expressed as a foreign protein, and wherein administration of the recombinant yeast creates a protective humoral immune response.

34. The method as claimed in claim 33, wherein the vaccine comprises complete yeast cells of the recombinant yeast and a specific immunization against the expressed foreign protein is obtained.

35. The method as claimed in claim 34, wherein the foreign protein is obtained from a pathogen or a tumor.

36. The method as claimed in claim 34, wherein the foreign protein derives from a parasite, a bacterium or a virus.

37. The method as claimed in claim 34, wherein the foreign protein is a cytotoxic antigen.

38. The method as claimed in claim 33, wherein the vaccine comprises complete yeast cells of the recombinant yeast and a humoral immunization against expressed foreign protein is obtained.

39. The method as claimed in claim 33, wherein the vaccine comprises complete yeast cells of the recombinant yeast and a protective humoral immunization against expressed foreign protein is obtained.

40. A method comprising detecting neutralizing antibodies from sera of individuals which were immunized by the method as claimed in claim 32.

41. The method as claimed in claim 40, wherein the neutralizing antibodies are against IBDV VP2 protein and/or mutated IBDV VP2-T2S protein and/or the codon-optimized oVP2-T2S protein.

42. A method comprising detecting the immunization effected by the method as claimed in claim 32 via challenge with antigen.

43. A method comprising detecting the immunization effected by the method as claimed in claim 32 via challenge with viral antigen or challenge with virus.

44. A method comprising detecting the immunization effected by the method as claimed in claim 32 via challenge with IBDV VP2 and/or mutated IBDV VP2-T2S and/or codon-optimized oVP2-T2S protein.

* * * * *

SEQUENCE LISTING

```
<160> NUMBER OF SEQ ID NOS: 10

<210> SEQ ID NO 1
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

atgacaaacc tgcaagatca aacccaacag attgttccgt tcatacggag ccttctgatg      60

ccaacaaccg gaccggcgtc cattccggac gacaccctgg agaagcacac tctcaggtca     120

gagacctcga cctacaattt gactgtgggg gacacagggt cagggctaat tgtctttttc     180

cctggattcc ctggctcaat tgtgggtgct cactacacac tgcagggcaa tgggaactac     240
```

-continued

```
aagttcgatc agatgctcct gactgcccag aacctaccgg ccagttacaa ctactgcagg    300

ctagtgagtc ggagtctcac agtgaggtca agcacacttc ctggtggcgt ttatgcacta    360

aacggcacca taaacgccgt gaccttccaa ggaagcctga gtgaactgac agatgttagc    420

tacaatgggt tgatgtctgc aacagccaac atcaacgaca aaattgggaa cgtcctagta    480

ggggaagggg tcaccgtcct cagcttaccc acatcatatg atcttgggta tgtgaggctt    540

ggtgacccca ttcccgcaat agggcttgac ccaaaaatgg tagccacatg tgacagcagt    600

gacaggccca gagtctacac cataactgca gccgatgatt accaattctc atcacagtac    660

caaccaggtg gggtaacaat cacactgttc tcagccaaca ttgatgccat cacaagcctc    720

agcgttgggg gagagctcgt gtttcaaaca agcgtccacg gccttgtact gggcgccacc    780

atctacctca taggctttga tgggacaacg gtaatcacca gggctgtggc cgcaaacaat    840

gggctgacga ccggcaccga caaccttatg ccattcaatc ttgtgattcc aacaaacgag    900

ataacccagc caatcacatc catcaaactg gagatagtga cctccaaaag tggtggtcag    960

gcaggggatc agatgtcatg gtcggcaaga gggagcctag cagtgacgat ccatggtggc   1020

aactatccag ggccctccg tcccgtcacg ctagtggcct acgaaagagt ggcaacagga   1080

tccgtcgtta cggtcgctgg ggtgagcaac ttcgagctga tcccaaatcc tgaactagca   1140

aagaacctgg ttacagaata cggccgattt gacccaggag ccatgaacta cacaaaattg   1200

atactgagtg agagggaccg tcttggcatc aagaccgtct ggccaacaag ggagtacact   1260

gactttcgtg aatacttcat ggaggtggcc gacctcaact ctcccctgaa gattgcagga   1320

gcattcggct tcaaagacat aatccgggcc ataaggagga tagctgtgtg a            1371
```

```
<210> SEQ ID NO 2
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160
```

-continued

```
Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val
    450                 455
```

<210> SEQ ID NO 3
<211> LENGTH: 1371
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 3

```
atgtctaacc tgcaagatca aacccaacag attgttccgt tcatacggag ccttctgatg      60

ccaacaaccg gaccggcgtc cattccggac gacaccctgg agaagcacac tctcaggtca     120

gagacctcga cctacaattt gactgtgggg gacacagggt cagggctaat tgtctttttc     180

cctggattcc ctggctcaat tgtgggtgct cactacacac tgcagggcaa tgggaactac     240

aagttcgatc agatgctcct gactgcccag aacctaccgg ccagttacaa ctactgcagg     300

ctagtgagtc ggagtctcac agtgaggtca agcacacttc ctggtggcgt ttatgcacta     360
```

-continued

```
aacggcacca taaacgccgt gaccttccaa ggaagcctga gtgaactgac agatgttagc    420

tacaatgggt tgatgtctgc aacagccaac atcaacgaca aaattgggaa cgtcctagta    480

ggggaagggg tcaccgtcct cagcttaccc acatcatatg atcttgggta tgtgaggctt    540

ggtgacccca ttcccgcaat agggcttgac ccaaaaatgg tagccacatg tgacagcagt    600

gacaggccca gagtctacac cataactgca gccgatgatt accaattctc atcacagtac    660

caaccaggtg ggtaacaat cacactgttc tcagccaaca ttgatgccat cacaagcctc    720

agcgttgggg gagagctcgt gtttcaaaca agcgtccacg gccttgtact gggcgccacc    780

atctacctca taggctttga tgggacaacg gtaatcacca gggctgtggc cgcaaacaat    840

gggctgacga ccggcaccga caaccttatg ccattcaatc ttgtgattcc aacaaacgag    900

ataacccagc caatcacatc catcaaactg gagatagtga cctccaaaag tggtggtcag    960

gcaggggatc agatgtcatg gtcggcaaga gggagcctag cagtgacgat ccatggtggc   1020

aactatccag ggccctccg tcccgtcacg ctagtggcct acgaaagagt ggcaacagga   1080

tccgtcgtta cggtcgctgg ggtgagcaac ttcgagctga tcccaaatcc tgaactagca   1140

aagaacctgg ttacagaata cggccgattt gacccaggag ccatgaacta cacaaaattg   1200

atactgagtg agagggaccg tcttggcatc aagaccgtct ggccaacaag ggagtacact   1260

gactttcgtg aatacttcat ggaggtggcc gacctcaact ctcccctgaa gattgcagga   1320

gcattcggct tcaaagacat aatccgggcc ataaggagga tagctgtgtg a            1371
```

<210> SEQ ID NO 4
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

```
Met Ser Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175
```

```
Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val
    450                 455
```

<210> SEQ ID NO 5
<211> LENGTH: 1371
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5

```
atgtccaact tacaagacca aacccaacaa atcgtccctt ttatcagatc cttattaatg      60

cctactaccg gtcctgcttc tattcctgat gacaccttgg aaaaacacac cttgagatcc     120

gaaacttcaa cctataactt gactgtcggt gacactggtt ctggtttaat cgttttcttc     180

cctggttttc ctggttcaat tgtcggtgcc cactatacct tacaaggtaa cggtaactat     240

aagttcgatc aaatgttgtt gaccgcccaa aatttgcctg cctcctataa ctattgtaga     300

ttggtttcta gatctttaac cgtcagatca tccactttgc ctggtggtgt ctatgctttg     360

aacggtacaa tcaacgctgt cacatttcaa ggttccttgt ccgaattgac cgatgtctcc     420
```

-continued

```
tataacggtt taatgtccgc tactgccaat atcaatgaca aaattggtaa cgtcttagtc    480

ggtgaaggtg ttactgtttt gagtttgcca acctcttatg acttgggtta tgtcagattg    540

ggtgacccta ttcctgctat cggtttagac ccaaaaatgg ttgccacttg tgactctagt    600

gatagaccaa gagtctatac catcactgct gccgatgact atcaattctc ctcccaatat    660

caacctggtg gtgtcactat caccttgttc tctgccaaca tcgacgctat aacatctttg    720

tccgtcggtg gtgaattggt attccaaacc tccgtccatg gtttagtatt gggtgccacc    780

atctatttga ttggtttcga cggtacaacc gtcattacta gagccgttgc tgccaacaat    840

ggtttaacca ctggtactga caacttgatg ccattcaact tggtaatccc taccaacgaa    900

atcacacaac caatcacatc catcaaattg gaaattgtca cctccaaatc cggtggtcaa    960

gccggtgacc aaatgtcatg gagtgctaga ggttcattag ccgtaaccat ccacggtggt   1020

aactatcctg gtgccttgag acctgtcact ttagtcgcct atgaaagagt tgctactggt   1080

tccgtcgtta ctgttgccgg tgtttcaaac ttcgaattga tcccaaaccc agaattggcc   1140

aaaaacttgg ttaccgaata tggtagattc gaccctggtg ctatgaacta tacaaaattg   1200

atcttatccg aaagagacag attgggtatc aaaactgtct ggcctactag agaatatacc   1260

gactttagag aatatttcat ggaagtcgcc gacttaaatt ccccattgaa aatcgccggt   1320

gcctttggtt ttaaggacat cattagagcc attagaagaa tagccgtctg a              1371


<210> SEQ ID NO 6
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Gly Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190
```

-continued

```
Met Val Ala Thr Cys Asp Ser Ser Asp Arg Pro Arg Val Tyr Thr Ile
        195                 200                 205

Thr Ala Ala Asp Asp Tyr Gln Phe Ser Ser Gln Tyr Gln Pro Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Gln Thr Ser Val His Gly Leu Val
                245                 250                 255

Leu Gly Ala Thr Ile Tyr Leu Ile Gly Phe Asp Gly Thr Thr Val Ile
            260                 265                 270

Thr Arg Ala Val Ala Ala Asn Asn Gly Leu Thr Thr Gly Thr Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Gly Gly Gln
305                 310                 315                 320

Ala Gly Asp Gln Met Ser Trp Ser Ala Arg Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Thr Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val
    450                 455
```

<210> SEQ ID NO 7
<211> LENGTH: 28
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ggcgcgccga tgacaaacct gcaagatc 28

<210> SEQ ID NO 8
<211> LENGTH: 38
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ataagaatgc ggccgctcac acagctatcc tccttatg 38

<210> SEQ ID NO 9

<211> LENGTH: 35
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
ggcgcgccga tgtctaacct gcaagatcaa accca 35

<210> SEQ ID NO 10
<211> LENGTH: 8157
<212> TYPE: DNA
<213> ORGANISM: Artificial Sequence
<220> FEATURE:
<223> OTHER INFORMATION: Description of Artificial Sequence: Synthetic plasmid vector

<400> SEQUENCE: 10
aggtggcact tttcggggaa atgtgcgcgg aacccctatt tgtttatttt tctaaataca 60
ttcaaatatg tatccgctca tgagacaata accctgataa atgcttcaat aatattgaaa 120
aaggaagagt atgagtattc aacatttccg tgtcgccctt attccctttt ttgcggcatt 180
ttgccttcct gtttttgctc acccagaaac gctggtgaaa gtaaaagatg ctgaagatca 240
gttgggtgca cgagtgggtt acatcgaact ggatctcaac agcggtaaga tccttgagag 300
ttttcgcccc gaagaacgtt ttccaatgat gagcactttt aaagttctgc tatgtggcgc 360
ggtattatcc cgtattgacg ccgggcaaga gcaactcggt cgccgcatac actattctca 420
gaatgacttg gttgagtact caccagtcac agaaaagcat cttacggatg gcatgacagt 480
aagagaatta tgcagtgctg ccataaccat gagtgataac actgcggcca acttacttct 540
gacaacgatc ggaggaccga aggagctaac cgcttttttg cacaacatgg gggatcatgt 600
aactcgcctt gatcgttggg aaccggagct gaatgaagcc ataccaaacg acgagcgtga 660
caccacgatg cctgtagcaa tggcaacaac gttgcgcaaa ctattaactg gcgaactact 720
tactctagct tcccggcaac aattaataga ctggatggag gcggataaag ttgcaggacc 780
acttctgcgc tcggcccttc cggctggctg gtttattgct gataaatctg gagccggtga 840
gcgtgggtct cgcggtatca ttgcagcact ggggccagat ggtaagccct cccgtatcgt 900
agttatctac acgacgggga gtcaggcaac tatggatgaa cgaaatagac agatcgctga 960
gataggtgcc tcactgatta agcattggta actgtcagac caagtttact catatatact 1020
ttagattgat ttaaaacttc atttttaatt taaaaggatc taggtgaaga tcctttttga 1080
taatctcatg accaaaatcc cttaacgtga gttttcgttc cactgagcgt cagaccccgt 1140
agaaaagatc aaaggatctt cttgagatcc tttttttctg cgcgtaatct gctgcttgca 1200
aacaaaaaaa ccaccgctac cagcggtggt ttgtttgccg gatcaagagc taccaactct 1260
ttttccgaag gtaactggct tcagcagagc gcagatacca aatactgtac ttctagtgta 1320
gccgtagtta ggccaccact tcaagaactc tgtagcaccg cctacatacc tcgctctgct 1380
aatcctgtta ccagtggctg ctgccagtgg cgataagtcg tgtcttaccg ggttggactc 1440
aagacgatag ttaccggata aggcgcagcg gtcgggctga acggggggtt cgtgcacaca 1500
gcccagcttg gagcgaacga cctacaccga actgagatac ctacagcgtg agctatgaga 1560
aagcgccacg cttcccgaag ggagaaaggc ggacaggtat ccggtaagcg gcagggtcgg 1620
aacaggagag cgcacgaggg agcttccagg gggaaacgcc tggtatcttt atagtcctgt 1680
cgggtttcgc cacctctgac ttgagcgtcg atttttgtga tgctcgtcag gggggcggag 1740

```
cctatggaaa aacgccagca acgcggcctt tttacggttc ctggcctttt gctggccttt   1800
tgctcacatg ttctttcctg cgttatcccc tgattctgtg gataaccgta ttaccgcctt   1860
tgagtgagct gataccgctc gccgcagccg aacgaccgag cgcagcgagt cagtgagcga   1920
ggaagcggaa gagcgcccaa tacgcaaacc gcctctcccc gcgcgttggc cgattcatta   1980
atgcagctgg cacgacaggt ttcccgactg gaaagcgggc agtgagcgca acgcaattaa   2040
tgtgagttag ctcactcatt aggcacccca ggctttacac tttatgctcc cggctcgtat   2100
gttgtgtgga attgtgagcg gataacaatt tcacacagga aacagctatg accatgatta   2160
cgccaagcgc gcaattaacc ctcactaaag ggaacaaaag ctgggtaccg ggcccgcgac   2220
ctaaccattc aaatgattca taactatctc ctagccagaa ttcgtaccca actcttggga   2280
aatcaggagg ctgatattcg ccagtaagct tcatagaagt gttcaagttt attttgttag   2340
caaagatcgt gtacttctga acagtctcaa acccatagta aaatacaact ggggatatac   2400
gagagttaac cgtgactaca gctagagaac cattagaacc tttttcgaca ctcactccat   2460
ggatgttttg cttcattaaa tcaatattgt acttcttcca gttcttaaag tccctaggtt   2520
catcattatt cgttggaggt ctccagaaag tgattgaaga accctcaaac ttgctggaaa   2580
tttccttacc cttgaccttt aggctttcaa ttttacccaa caatttgtcc aagataaaat   2640
gcaatccact ggattcaact gagacataac gtttaccgtc gttgatcttc gcagcttttt   2700
ctgctgtctc tgtaacaaaa tcgggtacct tcaatggaag ttcagcttgg ccccaggcaa   2760
tttcatgacc tgcctttaga acaccagcat catctttcaa cacggcaaca acataagttg   2820
tatcagaagg aatagtaaca gattcttctg gctttaaaga tggaacgtcg attgtctttc   2880
ccgtgtcctt gtcgataaac aataagtggt ctgtcgtaat gaagtcgtgc ttatttgtga   2940
ttgttacaga tccgtgcgca attttaatat gaacgggttc aataaccttc ttatactcta   3000
caaggcccgg agtaggatta tgctcactgt tacacaaacc atccatgatg aacactccgt   3060
catgaacctc ttccttaaag tcaccaccat aagcataagc tttatgcaac ttaccatctg   3120
cagtactaac atcttcgaat tcaataccgt gatttgccca ttcccagata aagccacctt   3180
ggtaaaactt ctccttgtag aacaactctt gatattcttt caaagagcca ggaccgttac   3240
ccattgcatg gccgtactca cacaagatca aaggcttttc aaacttacca ttttcatcag   3300
tgtggttctt cctccacctt tccataattt caaatgttgg gtacatgaaa ctaaagatat   3360
ctgcactcaa agcgttcaag tcaccctcat aatgcacaag tctggtagga tccaattgtt   3420
taattaactt gtacatggct ttgtggtttc tgccataaca agcttcgtta cccaaggacc   3480
agataataat cgaaggatga ttgacatctc ttaggacaag ttgggaagct ctgtctaagt   3540
acgcgacctc gtactctgga ttatctgata agtaatgggc attaacatcg tagagtttat   3600
ttttagtatc tggatattca gcctccaagt tcgtatgacg attaaatggc tcttgaacac   3660
catgagtttc aagatctgcc tcgtcaatga cccagaagcc cagcttatcg aagaggtcat   3720
acaccttagg atggtttgga taatgcgagt tacgaacagc attgatgtta aacttcttca   3780
ttagaatcaa gtccctaaca acaaaatcta atggcacagc tctaccgaac cttggatggt   3840
gatcatgtct gttgacacct ctaaagagaa tgtctttgcc attaacagta atgttaccgt   3900
ccttcaactc cacttgtctg aaaccaacat ggtgcttaat agattgaatc acactgccat   3960
cagatccaat taaatccaac tggtacttgt acaaagtagg attttctgcg gtccaatgtt   4020
ctggggcctt gacgttgatc ttgaaagctg tttcttcgtt ctttttggtg gagaaggaaa   4080
```

-continued

```
taaattcttt agttgaaaaa gtcgtgttcc cattctcctc gttcaacaaa gagcttgcat   4140
cgtaaacttt agatccatct tcaggttcgt aaagtgtgaa attgatgtga tcataagaag   4200
aaccctggac atcaactttc acagaaagct ctgcatcctg atactgagag tccacaaaag   4260
ttgtagtgac cctaacgtct tcaatatggg ccttcttagg caattttagt aaagaaacgt   4320
ctctgtaaat accagagagc caccattgat cttggtcctc gatataagtg gaatcggacc   4380
acttgaaaac cttgacgacc actaagtttt cgccctcaga aacgtacttt tggatatcaa   4440
attcagcccc gttacgggac cccttattga aacccacata ttgaccatta acataaagct   4500
cgtaacaatt gtccacaccc tcaaatctca atctgtgctc gaacgactca atcgatttcg   4560
aatctaattc aaaagttcta gcataaacac cagtaggatt tacagtggga ggatttggga   4620
tgtcgattgg gatagggtac tgtacgttcg tgtaaattgg tttaccgtac ttccagtctt   4680
cctgaagttc ccaatgggat ggcacagaaa tggtgctcca tttctttgcc gtttcccagt   4740
ctaaattctt agcatccgga gcgtcaagag gtgcatcaaa caacgcaaaa gcccaaggcc   4800
cattgagaga ttcgaaaata tcctgatcat agtagtaagc cctagtaggc aatctatttt   4860
cgtgaacctt tttggggttc cttaaattct caggaataag gcaagccatg gtgccgtcct   4920
gccgagatat tgtgtacact ggatcaaata ataacacttt caaagtgact aaatcacaat   4980
tgtcccaaga tatactatag ctctctgttt aacctttata ttgtcaaaaa gggacaatga   5040
atgaaagtac aaacacaaac acaaacacaa tggaagggag tgtccagggt ggtgattcct   5100
gactgtactg attcgacgga gttttatttg atttcgttga agtggttaaa gtgaataatt   5160
cttgaattga gaggaacaaa gagtggataa aataacggaa tggagaggtc cgagcgatga   5220
ataatgtacg attcggaaga ctatgagccg gctgaacctg aggttatgga ccactaacgt   5280
cctggttgac aagagtagtc atgtaataca aacgtaaatg tgatatttaa tagaatataa   5340
gtagatatag ttaaaaagaa gaagaagaat agaaagaata agggtattag aaatttagag   5400
tcattttaaa caattgataa cttgggttaa agctcgaagt tttgttgata gtagtttttt   5460
tttttgtttt agttggtttg ttcaatagta taaggttaca gggtgcgaga caaacgttgt   5520
aacacttttc atctcccccc gctaatcacc tagtcgagag ctcgttttcg acactggatg   5580
gcggcgttag tatcgaatcg acagcagtat agcgaccagc attcacatac gattgacgca   5640
tgatattact ttctgcgcac ttaacttcgc atctgggcag atgatgtcga ggcgaaaaaa   5700
aatataaatc acgctaacat ttgattaaaa tagaacaact acaatataaa aaaactatac   5760
aaatgacaag ttcttgaaaa caagaatctt tttattgtca gtactgagtc gaggcggccg   5820
ctggccaccc gggtctagag gcgcgccgtc gacggtacag cttctcgatg agtatgtgtg   5880
tttatttttt ttttattttt tttgccaaat tctgctcttt cctaaatttc aagtgttgag   5940
cttgttatcc gctcacaatt ccagcttttg tctcttcacc ttttccaact acaagcgcaa   6000
cataacaaaa gaataataat tctcctaaga aacacaagcc tcatatacct ttcgagttag   6060
ggaagaacat cttctctcat gatacacatt gattcgagct attaaatacc tttttctcaa   6120
tcgaaatctc aagtaaaaca gcaatgaaaa cattacgtaa ctaaaggtgt tcaccactag   6180
aaatcatacc cttcacactc gacttcaagt agtgaatggt gtagcaacaa agtccaaata   6240
ccaatgtcaa ccaagtaacc gaccgcacta ctagaaaaag acgctgttgc tcggaccaca   6300
aatttccgct acacttttca caactatact gaagatacaa aaaacgtgtg tgggtatggc   6360
tggctaccag gtcgcctggt taaaccaagt caacgtgata catatgtacg ttccaacact   6420
aagcctaccc taagtttcgg ctcacaggct aggctattat taacatgcaa gacaagggag   6480
```

-continued

```
aagcaaagca aagaccaacc gaaacccacc agagcaccct gaactttgcg gtgaacagaa   6540
ttccgcaaca tatctgagga taccatgatc tcgttttcct actccatatg ggaatcaccc   6600
actgttgtcc gtaaatatga ccaaattcct accttgattc ctcacgaata atcgcagtcc   6660
gaaaagccgt tccaaaagcc agtccacagt ccatcaattg gtatgatgat tgtttttttg   6720
ttcaaactga cacactaacg gtgtggaatg cgaagagtga gcttaccctt ctcctctttg   6780
ctagcagtac ttgcctacct acctactcta ctacgctgcc atattgtcta acattcggct   6840
ttctctattt ctacctggcc tggatggctc cgtctcgccc gcctcacaca catacattcc   6900
tccccctctc gcctgcccca taataattaa acaagttaac aaaaggcgtt acctcttccg   6960
catcctctcc aatctcatac gattcccctt tcatccgact tacccaacaa gatacaggat   7020
ctcagtgaaa gatccttcct gccctccctg tctgttgtct actctacatg cgacttggaa   7080
ggccaaagga ctatcgcatg attattcgcc gggaacccgc gagttccctg ctcttttctt   7140
tcaaaccagg cagcaaacca ggtgaacaca ctctgatgta gtgcagtccc taagtccttt   7200
gaagattcgg ggagctagct acccacgcga atgtaacaaa agaacattta cttttgtggg   7260
gggtggaaaa gtcgattagg atcttgcagc acagaaactg cgcaggggtt tttttcatct   7320
tggagaagca actggctaaa ttcgacacaa acaaaaactg aaaaatggaa aataaaaaat   7380
gaaaaagcaa gctgaattcg aagaagggag aattccgcct tctgcaacca cactaatggt   7440
tggtagtcaa tagatacgca ttagaaggtt actattttat gagtcgatcc ccgcggtgga   7500
gctccaattc gccctatagt gagtcgtatt acgcgcgctc actggccgtc gttttacaac   7560
gtcgtgactg ggaaaaccct ggcgttaccc aacttaatcg ccttgcagca catccccctt   7620
tcgccagctg gcgtaatagc gaagaggccc gcaccgatcg cccttcccaa cagttgcgca   7680
gcctgaatgg cgaatggcgc gacgcgccct gtagcggcgc attaagcgcg gcgggtgtgg   7740
tggttacgcg cagcgtgacc gctacacttg ccagcgccct agcgcccgct cctttcgctt   7800
tcttcccttc ctttctcgcc acgttcgccg gctttccccg tcaagctcta aatcgggggc   7860
tccctttagg gttccgattt agtgctttac ggcacctcga ccccaaaaaa cttgattagg   7920
gtgatggttc acgtagtggg ccatcgccct gatagacggt ttttcgccct ttgacgttgg   7980
agtccacgtt ctttaatagt ggactcttgt tccaaactgg aacaacactc aaccctatct   8040
cggtctattc ttttgattta taagggattt tgccgatttc ggcctattgg ttaaaaaatg   8100
agctgattta acaaaaattt aacgcgaatt ttaacaaaat attaacgctt acaattt      8157
```